United States Patent [19]

Ebetino

[11] Patent Number: 5,574,024
[45] Date of Patent: Nov. 12, 1996

[54] METHYLENE PHOSPHONOALKYLPHOSPHINATES, PHARMACEUTICAL COMPOSITIONS, AND METHODS FOR TREATING ABNORMAL CALCIUM AND PHOSPHATE METABOLISM

[76] Inventor: Frank H. Ebetino, Norwich Eaton Pharmaceuticals, Inc., Woods Corners, P.O. Box 191, Norwich, N.Y. 13815-0191

[21] Appl. No.: 253,818

[22] Filed: Jun. 3, 1994

Related U.S. Application Data

[63] Continuation of Ser. No. 672,149, Mar. 19, 1991, abandoned, which is a continuation of Ser. No. 69,666, Jul. 6, 1987, abandoned.

[51] Int. Cl.⁶ .................... A61K 31/44; A61K 31/445; C07F 9/58; C07F 9/59
[52] U.S. Cl. ................ 514/89; 546/21; 546/22; 546/23
[58] Field of Search ................ 546/21, 22, 23; 514/89

[56] References Cited

U.S. PATENT DOCUMENTS

| | | | |
|---|---|---|---|
| 3,553,314 | 1/1971 | Francis | 424/49 |
| 3,683,080 | 8/1972 | Francis | 514/107 |
| 3,846,420 | 11/1974 | Wollmann et al. | 455/157 |
| 3,899,496 | 8/1975 | Schindler et al. | 546/22 |
| 3,941,772 | 3/1976 | Polger et al. | 546/6 |
| 3,957,160 | 5/1976 | Ploger et al. | 210/58 |
| 3,979,385 | 9/1976 | Wollmann et al. | 548/412 A |
| 3,988,443 | 10/1976 | Ploger et al. | 544/157 |
| 4,113,861 | 9/1978 | Fleisch et al. | 514/79 |
| 4,117,090 | 9/1978 | Ploger | 423/268 |
| 4,134,969 | 1/1979 | Schmidt-Dunker | 424/49 |
| 4,267,108 | 5/1981 | Blum et al. | 548/413 |
| 4,304,734 | 12/1981 | Jary et al. | 562/13 |
| 4,407,761 | 10/1983 | Blum et al. | 562/13 |
| 4,469,686 | 9/1984 | Andrews | 514/92 |
| 4,608,368 | 8/1986 | Blum et al. | 514/107 |
| 4,621,077 | 11/1986 | Rosini et al. | 514/108 |
| 4,687,767 | 8/1987 | Bosies et al. | 514/89 |
| 4,687,768 | 8/1987 | Benedict et al. | 514/102 |
| 4,711,880 | 12/1987 | Stahl et al. | 514/108 |
| 4,719,203 | 1/1988 | Bosies et al. | 514/108 |

FOREIGN PATENT DOCUMENTS

| | | |
|---|---|---|
| 88359 | 9/1983 | European Pat. Off. . |
| 100718 | 2/1984 | European Pat. Off. . |
| 186405 | 7/1986 | European Pat. Off. . |
| 197478 | 10/1986 | European Pat. Off. . |
| 230068 | 7/1987 | European Pat. Off. . |
| 273514 | 7/1988 | European Pat. Off. . |
| 274158 | 7/1988 | European Pat. Off. . |
| 2104476 | 8/1972 | Germany . |
| 2343147 | 4/1975 | Germany . |
| 2360798 | 6/1975 | Germany . |
| 2513966 | 10/1976 | Germany . |
| 2541981 | 3/1977 | Germany . |
| 3334211 | 4/1985 | Germany . |
| 53-59674 | 5/1978 | Japan . |
| 54-135724 | 10/1979 | Japan . |
| 55-98193 | 7/1980 | Japan . |
| 8703598 | 6/1987 | WIPO . |

OTHER PUBLICATIONS

H. G. Henning et al., "Methylene–bis–phosphonic Acid Ester and Methylene–bis–phosphinic Acid Ester", 5 Z. Chem. 419 (1965).
A. N. Pudovik et al., "Reactions of Acid Ethylphosphonous and Phosphorothious Esters with Carbonylphosphonic Esters and 2,3–Butanedione", 37 Z. Obs. Khim. 876 (1967).
A. N. Pudovik et al., "Phosphonate–phosphate Rearrangement of Esters of Hydroxyalkylphosphonic Acids", Z. Obs. Khim. 143 (1968).
A. N. Pudovik et al., "Synthesis and Reactions of (2–Cyanovinyl)phosphonic Esters", 38 Z. Obs. Khim. 292 (1968).
W. Ploger et al., "Preparation of 1–Aminoalkane–1,1–diphosphonic Acids", 389 Z. Anorg. Allg. Chem. 119 (1972).
W. F. Gilmore et al., "Base–catalyzed Condensation of Aldehydes with Ethyl Bis(diethylphosphonomethyl)phosphinate", 38 J. Org. Chem. 1423 (1973).
G. V. Romanov et al., "Thermodynamic and Kinetic Characteristics of Phosphonate–Phosphate Rearrangement", 43 Z. Obs. Khim. 2378 (1973).
Z. S. Zovikova et al., "Addition of Tetraethyl Pyrophosphite and of Tetraethyl Isohypophosphate to Compounds Containing an Activated Double Bond", 44 Z. Obs. Khim. 276 (1974).
Z. S. Zovikova et al., "Reactions of Methyl Bis(diethoxy--phosphino)acetate with Alkyl Halides", 48 Z. Obs. Khim. 757 (1978).
J. Oleksyszyn et al., "Phosphoranaloge von Aminosauren und Peptiden: Phosphon–und Phosphinanaloge von Cycloleucin", 32 Chimia 253 (1978).
L. Maier, "Herstellung und Eigenschaften von Aminomethylendiphosphinaten und –diphosphonaten, $RR^1NCH[P(O)R^2(OR^3)]_2$ und Derivitaen", 11 Phosphorus und Sulfur 311 (1981).
L. Maier, "Advances in the Chemistry of Aminophosphinic Acids", 14 Phosphorus and Sulfur 295 (1983).
Francis et al., "Chemical, Biochemical, and Medicinal Properties of the Diphosphonates", The Role of Phosphonates in Living Systems, 55 (Hildebrand, ed., 1983).
Y. Surh et al., "Technetium–99m Labeled Phosphonic Acid Analog of Serine: Bone Uptake", 27 J. Nuclear Medicine, 847 (1986).
W. F. Gilmore et al., "Base–catalyzed Condensation of Bis(diethylphosphono–methyl)–phosphinic Amides with Aldehydes", 29 Phosphorus and Sulfur, 287 (1987).

Primary Examiner—Alan L. Rotman

[57] ABSTRACT

The present invention involves novel methylene phosphonoalkylphosphinic acids, pharmaceutical compositions containing such compounds, and methods for treating or preventing pathological conditions characterized by abnormal calcium and phosphate metabolism by administering such compounds to a human or lower animal.

26 Claims, No Drawings

METHYLENE PHOSPHONOALKYLPHOSPHINATES, PHARMACEUTICAL COMPOSITIONS, AND METHODS FOR TREATING ABNORMAL CALCIUM AND PHOSPHATE METABOLISM

This is a continuation of application Ser. No. 07/672,149, filed Mar. 19, 1991, now abandoned, which is a continuation of application Ser. No. 07/069,666, filed Jul. 6, 1987, abandoned.

TECHNICAL FIELD

The present invention relates to novel compounds which are methylene phosphonoalkylphosphinic acid, salt or ester compounds. The present invention further relates to pharmaceutical compositions which contain methylene phosphonoalkylphosphinic acid compounds, or the pharmaceutically-acceptable salt or ester thereof. Finally, the present invention relates to a method for treating or preventing diseases characterized by abnormal calcium and phosphate metabolism by utilizing a compound or pharmaceutical composition of the present invention.

BACKGROUND OF THE INVENTION

Certain methylene phosphonoalkylphosphinate compounds are disclosed in the following references: Gilmore, W. F., & J. W. Huber, "Base-Catalized Condensation of Aldehydes with Ethyl Bis(diethylphosphonomethyl)phosphonate", *Journal of Organic Chemistry*, Volume 38, No. 7 (1973), pp. 1423–1424; Gilmore, W. F., & J. S. Park, "Base-Catalized Condensation of Bis(diethylphosphonomethyl)phosphinic Amides with Aldehydes", *Phosphorus and Sulfur*, Volume 29 (1987), pp. 287–292; Aboujaoude, E. E., N. Collignon & P. Savignac, "Synthesis of Beta-carbonyl Phosphinates", *Journal of Organometallic Chemistry*, Volume 264 (1984), pp. 9–17; Henning, H. G., & G. Petzold, "Methylene-bis-phosphonic Acid Ester and Methylene-bis-phosphinic Acid Ester", *Z. Chem.*, Volume 5, No. 11 (1965), pp. 419–420; Abramov, V. S., & V. I. Barabanov, "Reaction of Phosphinic Acids with Aldehydes and Ketones, XXVII." *Zhurnal Obshchei Khimii*, Volume 36, No. 10 (1966), pp. 1830–1834; Abramov, V. S., V. I. Barabanov & L. I. Long, "Reactions of Phosphinic Acids with Aldehydes and Ketones, XXXII." *Zhurnal Obshchei Khimii*, Volume 37, No. 3 (1967), pp. 714–718; Pudovik, A. N., I. V. Gur'yanova, L. V. Banderova & M. G. Limin, "Reaction of Partial Esters of Ethylphosphinic and Phosphorothioic Acids with Alpha-oxo Phosphonic Acid Esters and Diacetyl", *Zhurnal Obshchei Khimii*, Volume 37, No. 4 (1967), pp. 876–881; Pudovik, A. N., I. V. Gur'yanova & M. G. Zimin, "Reactions of Phosphorus Acid, Ethylphosphinic Acid, and Thiophosphorus Acid Esters with some Substituted Benzoyl Phosphates", *Zhurnal Obshchei Khimii*, Volume 37, No. 11 (1967), pp. 2580–2585; Pudovik, A. N., I. V. Gur'yanova, L. V. Banderova & G. V. Romanov, "Phosphonatephosphate Rearrangement of Esters of Alpha-hydroxyalkylphosphonic Acids", *Zhurnal Obshchei Khimii*, Volume 38, No. 1 (1968), pp. 143–150; Pudovik, A. N., G. E. Yastrebova, V. I. Nikitina & Y. Y. Samitov, "Synthesis and Reactions of Esters of (Beta-cyanovinyl)phosphonic Acid", *Zhurnal Obshchei Khimii*, Volume 38, No. 2 (1968), pp. 292–299; Romanov, G. V., M. S. Yafarov, A. I. Konovalov, A. N. Pudovik, I. V. Konovalova & T. N. Yusupova, "Thermodynamic and Kinetic Characteristics of the Phosphonate-phosphate Rearrangement", *Zhurnal Obshchei Khimii*, Volume 43, No. 11 (1973), pp. 2378–2386; Novikova, Z. S., S. N. Mashoshina & I. F. Lutsenko, "Addition of Tetraethyl Pyrophosphite and Tetraethyl Isohypophosphate to Compounds with Activated Multiple Bonds", *Zhurnal Obshchei Khimii*, Volume 44, No. 2 (1974), pp. 276–281; Novikova, Z. S., A. A. Prishchenko & I. F. Lutsenko, "Synthesis of 1,3-Di(oxoalkoxyphospha)cycloalkanes", *Zhurnal Obshchei Khimii*, Volume 47, No. 11 (1977), pp. 2636–2637; Novikova, Z. S., S. Y. Skorobogatova & I. F. Lutsenko, "Reaction of Tetraethyl Carbomethoxymethylene-1,1-diphosphonite with Alkyl Halides", *Zhurnal Obshchei Khimii*, Volume 48, No. 4 (1978), pp. 757–764. These references are hereby incorporated herein in their entirety.

A number of pathological conditions which can afflict humans and lower animals involve abnormal calcium and phosphate metabolism. Such conditions may be divided into two broad categories:

(1) Conditions which are characterized by anomolous mobilization of calcium and phosphate leading to general or specific bone loss, or excessively high calcium and phosphate levels in the fluids of the body, such as osteoporosis and Paget's disease. Such conditions are sometimes referred to herein as pathological hard tissue demineralizations.

(2) Conditions which cause or result from deposition of calcium and phosphate anomolously in the body, such as arthritis. These conditions are sometimes referred to herein as pathological calcifications.

A variety of polyphosphonic acid derivatives, especially diphosphonic acid derivatives, have been proposed for use in the treatment and prophylaxis of diseases involving abnormal calcium and phosphate metabolism. For example, polyphosphonic acid compounds are disclosed in U.S. Pat. No. 3,683,080, issued Aug. 8, 1972 to Francis; U.S. Pat. No. 4,330,537, issued Oct. 28, 1980 to Francis; U.S. Pat. No. 4,267,108, issued May 12, 1981 to Blum et al.; and Francis and Martodam, "Chemical, Biochemical, and Medicinal Properties of the Diphosphonates" in *The Role of Phosphonates in Living Systems* (CRC Press; Hilderbrand, Editor), pp. 55–96(1983); the disclosure of all these publications being incorporated herein by reference.

Certain substituted phosphinic acids are disclosed to be useful for the treatment of inflammatory conditions, including arthritis, in U.S. Pat. No. 4,469,686 issued to Andrews on Sep. 4, 1984.

In spite of the above and much other research into the use of polyphosphonates to treat bone-metabolism diseases, there continues to be a need for new bone-active agents. The object of the present invention is therefore to provide a new class of bone-active compounds. It is a further object of the present invention to provide bone-active agents having low toxicity. Furthermore, an object of the present invention is to provide new bone-active compounds with favorable therapeutic indices. It is a further object of the present invention to provide pharmaceutical compositions useful for the treatment and prophylaxis of abnormal calcium and phosphate metabolism. In addition, it is an object of the present invention to provide methods for treating or preventing diseases characterized by abnormal calcium and phosphate metabolism in humans or lower animals.

These and other objects of the present invention will be apparent from the detailed disclosure of the present invention provided hereinafter.

SUMMARY OF THE INVENTION

The present invention relates to bone active methylene phosphonoalkylphosphinic acids, and the pharmaceutically-acceptable salts and esters thereof, having the general structure:

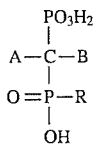

R is selected from hydrogen, and substituted and unsubstituted alkyl. A and B are substituent moieties. The most preferred A moiety is selected from pyridinyl-containing moieties, piperidinyl-containing moieties, and piperidinylidene-containing moieties. The most preferred B moiety is selected from hydrogen, hydroxy and amino. Also preferred is the A and B moieties covalently linked in a 5 carbon atom.ring.

The present invention further relates to pharmaceutical compositions containing a safe and effective amount of a methylene phosphonoalkylphosphinate compound of the present invention, and a pharmaceutically-acceptable carrier.

Finally, the present invention relates to methods for treating or preventing pathological conditions characterized by abnormal calcium and phosphate metabolism in humans or lower animals. This method comprises administering to a human or lower animal in need of such treatment a safe and effective amount of a compound or composition of the present invention.

DETAILED DESCRIPTION OF THE INVENTION

Bone Active Methylene Phosphonoalkylphosphinate Compounds

The compounds of the present invention are bone active methylene phosphonoalkylphosphinic acids, and the pharmaceutically-acceptable salts and esters thereof, having the general structure:

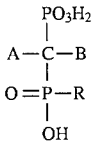 (1)

wherein the A, B, and R moieties are as defined hereinafter.

Compounds of the present invention bind with polyvalent metal ions, particularly di- and tri- valent metal ions (e.g., calcium and iron). Due to this binding property, especially with calcium, compounds of the present invention have affinity for bone and other calcified tissues. The affinity of compounds of the present invention for calcified tissues is demonstrated by use of the hydroxy apatite crystal growth inhibition test (See Example 3). Based on their affinity for bone and other calcified tissues, compounds of the present invention may be useful for one or more of a number of different therapeutic or diagnostic pharmacological uses.

Based on their affinity for bone and other calcified tissues, some compounds of the present invention are useful for carrying other agents to bone or other calcified tissues, or to tissues in the vicinity of bone or other calcified tissues, for therapeutic or diagnostic purposes. For example, some compounds of the present invention are useful as bone scanning agents after labeling with 99m-Technetium. Anti-infectives, anticancer drugs, antihelminthic drugs, antiinflammatory drugs, etc., may be attached to or complexed with some compounds of the present invention and be transported to bone or other calcified tissues to concentrate their activity in those or nearby tissues.

Compounds of the present invention are useful for treating or preventing pathological conditions characterized by abnormal calcium and phosphate metabolism. For example, some compounds of the present invention are useful in preventing calcification of tissues and of devices implanted into the human body (e.g. heart valves, vascular prostheses, hip prostheses, etc.). A use of some compounds of the present invention of particular interest is their use for preventing resorption of bone. The ability of compounds of the present invention to prevent bone resorption is determined by use of the thyroparathyroidectomized rat model (See Example 1) and the Schenk model (See Example 2). In addition, some compounds of the present invention may be useful in preventing the formation of tartar (i.e., calculus) and/or plaque on teeth.

Based on their property of binding with polyvalent metal ions, compounds of the present invention have other potential uses as sequestering agents for such ions. Thus, some compounds of the present invention are useful as builders in detergents and cleansers, or for treating water.

Some compounds of the present invention may also be useful as stabilizers for certain per compounds. Some compounds of the present invention may be useful as herbicides which are non-toxic to animals. Some compounds of the present invention may be useful as flame retardants.

The term "alkyl", as used herein, unless otherwise specified, means chemically-stable carbon-containing chains which may be straight, branched, or cyclic; and further which may be saturated, monounsaturated (e.g., one double bond; one triple bond), or polyunsaturated (e.g., two double bonds; two triple bonds; three double bonds; one double and one triple bond). Preferred alkyl have from 1 to about 20 carbon atoms, more preferred alkyl have from 1 to about 10 carbon atoms, and more preferred still alkyl have from 1 to about 6 carbon atoms. Still more preferred alkyl have from 1 to 4 carbon atoms, most preferred alkyl have 1 or 2 carbon atoms. "Cycloalkyls" as used herein, having from about 4 to about 10 carbon atoms are preferred; more preferred are cycloalkyls having 5 or 6 carbon atoms. Also preferred are straight chain alkyl, saturated alkyl or monounsaturated alkyl. Most preferred are straight chain, saturated alkyl.

Alkyl is preferably unsubstituted but may be substituted. Preferred substituent groups for alkyl are as follows: halogen; nitro; cyano; heterocycle; aryl; heteroaryl; unsubstituted amino, and the amide thereof derived from a carboxylic acid of an alkyl, heterocycle, aryl or heteroaryl group; amino Substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —$SO_3H$, the pharmaceutically-acceptable salts thereof, the ester thereof derived from an alcohol of an alkyl group, the unsubstituted amide thereof, and the amide thereof substituted with one or two alkyl groups; —$CO_2H$, the pharmaceutically-acceptable salts thereof, the ester thereof derived from an alcohol of an alkyl group, the unsubstituted amide thereof, and the amide thereof substituted with one or two alkyl groups; $PO_3H_2$, the pharmaceutically-acceptable salts thereof, the ester thereof derived from an alcohol of an alkyl group, the unsubstituted amide thereof, and the amide thereof substituted with one or two alkyl groups; —(R⁸)PO₂H (where R⁸ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof. More preferred alkyl substituents are halogen, especially fluoro; trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; amino substituted independently with two lower alkyl groups; peptidyl having from one to about six amino acid moieties; and chemically-stable combinations thereof.

The term "lower alkyl", as used herein, unless otherwise specified, means unsubstituted alkyl having from 1 to about 6 carbon atoms which may be saturated or unsaturated. Preferred lower alkyl have from one to about 4 carbon atoms; more preferred lower alkyl have one or two carbon atoms. Preferred lower alkyl are saturated. Most preferred lower alkyl are methyl and ethyl. For lower alkyl groups specified herein as substituted, preferred substituents are the same as for alkyl hereinabove.

The term "heterocycle", as used herein, unless otherwise specified, means chemically-stable non-aromatic rings, including fused non-aromatic rings, having from about 5 to about 20 atoms, comprising at least one heteroatom selected from nitrogen, sulfur, phosphorus and oxygen. Preferred are 5 and 6 membered ring heterocycles which comprise from about 1 to about 3 heteroatoms. More preferred are 5 and 6 membered ring heterocycles which comprise one or two heteroatoms (especially nitrogen hetero-atoms). Most preferred are the 6 membered ring heterocycles comprising one nitrogen atom, especially piperidinyl and piperidinylidene heterocycles. Heterocycles may be unsubstituted or substituted, saturated or unsaturated. Preferred heterocycles are unsubstituted or substituted with alkyl; halogen; nitro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —SO₃H, the pharmaceutically-acceptable salts thereof, the ester thereof derived from an alcohol of an alkyl group, the unsubstituted amide thereof, and the amide thereof substituted with one or two alkyl groups; —CO₂H, the pharmaceutically-acceptable salts thereof, the ester thereof derived from an alcohol of an alkyl group, the unsubstituted amide thereof, and the amide thereof substituted with one or two alkyl groups; PO₃H₂, the pharmaceutically-acceptable salts thereof, the ester thereof derived from an alcohol of an alkyl group, the unsubstituted amide thereof, and the amide thereof substituted with one or two alkyl groups; —(R⁸)PO₂H (where R⁸ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof. More preferred heterocycles are unsubstituted or substituted with lower alkyl; halogen, especially fluoro; trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; amino substituted independently with two lower alkyl groups; peptidyl having from one to about six amino acid moieties; and chemically-stable combinations thereof.

The term "aryl", as used herein unless otherwise specified, means chemically-stable aromatic rings, including fused aromatic rings, having from about 6 to about 20 carbon atoms. Preferred aryl are phenyl or naphthyl; most preferred is phenyl. Aryls may be unsubstituted or substituted. Preferred aryls are unsubstituted or substituted with alkyl; halogen; nitro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —SO₃H, the pharmaceutically-acceptable salts thereof, the ester thereof derived from an alcohol of an alkyl group, the unsubstituted amide thereof, and the amide thereof substituted with one or two alkyl groups; —CO₂H, the pharmaceutically-acceptable salts thereof, the ester thereof derived from an alcohol of an alkyl group, the unsubstituted amide thereof, and the amide thereof substituted with one or two alkyl groups; PO₃H₂, the pharmaceutically-acceptable salts thereof, the ester thereof derived from an alcohol of an alkyl group, the unsubstituted amide thereof, and the amide thereof substituted with one or two alkyl groups; —(R⁸)PO₂H (where R⁸ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; aldehyde; ketone having an alkyl group carbamate, unsubstituted or substituted with one or two alkyl groups; peptidyl; and combinations thereof. More preferred aryl are unsubstituted or substituted with lower alkyl; halogen, especially fluoro; trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; amino substituted independently with two lower alkyl groups; peptidyl having from one to about six amino acid moieties; and chemically-stable combinations thereof.

The term "heteroaryl" as used herein unless otherwise specified, means chemically-stable aromatic rings, including fused aromatic rings and fused aromatic and non-aromatic rings, having from about 5 to about 20 atoms, comprising at least one hetero-atom selected from nitrogen, sulfur, phosphorus and oxygen. Preferred are 5 and 6 membered ring heteroaryls which comprise from about 1 to about 3 heteroatoms. More preferred are 5 and 6 membered ring heteroaryls which comprise one or two heteroatoms (especially nitrogen heteroatoms). Most preferred heteroaryl is pyridinyl. Heteroaryls may be unsubstituted or substituted. Preferred heteroaryls are unsubstituted or substituted with alkyl; halogen; nitro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —$SO_3H$, the pharmaceutically-acceptable salts thereof, the ester thereof derived from an alcohol of an alkyl group, the unsubstituted amide thereof, and the amide thereof substituted with one or two alkyl groups; —$CO_2H$, the pharmaceutically-acceptable salts thereof, the ester thereof derived from an alcohol of an alkyl group, the unsubstituted amide thereof, and the amide thereof substituted with one or two alkyl groups; $PO_3H_2$, the pharmaceutically-acceptable salts thereof, the ester thereof derived from an alcohol of an alkyl group, the unsubstituted amide thereof, and the amide thereof substituted with one or two alkyl groups; —$(R^8)PO_2H$ (where $R^8$ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof. More preferred heteroaryls are unsubstituted or substituted with lower alkyl; halogen, especially fluoro; trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; amino substituted independently with two lower alkyl groups; peptidyl having from one to about six amino acid moieties; and chemically-stable combinations thereof.

The term "chemically-stable", as used herein, refers to compounds which are sufficiently stable under normal storage and use conditions such that they can provide the intended uses as described herein. The compounds, compositions and methods of use of the present invention include only chemically-stable compounds. Compounds having combinations of substituents and/or moieties which would result in chemically-unstable compounds are not included in the compounds of the present invention. Such chemically-unstable compounds which might otherwise fall within the descriptions of the compounds of the present invention are readily identified by a skilled chemist.

The term "substituent group", as used herein, means hydrogen or an alkyl, heterocycle, aryl or heteroaryl group, unless otherwise specified.

R is a moiety selected from the group consisting of hydrogen, and alkyl. Preferred R is unsubstituted alkyl, especially lower alkyl. Preferred substituents on the R alkyl, when substituted, include halogen, unsubstituted and substituted phenyl, unsubstituted and substituted pyridinyl, unsubstituted amino, amino substituted with one or two lower alkyl groups, hydroxy, carboxy, and chemically-stable combinations thereof. More preferred substituents are fluoro, phenyl, unsubstituted amino, and hydroxy; and most preferred are fluoro (especially when present as trifluoromethyl) and phenyl.

Particularly preferred R moieties are selected from unsubstituted lower alkyl groups, especially unsubstituted, straight-chain, saturated lower alkyl groups. Also preferred R moieties are selected from methyl, ethyl, n-propyl, iso-propyl, n-butyl, iso-butyl, sec-butyl, tert-butyl, and n-hexyl. More preferred still R moieties are selected from methyl, ethyl, n-propyl, and n-butyl. Most preferred R moiety is methyl.

A is a moiety selected from the group consisting of hydrogen; halogen; nitro; alkyl; heterocycle; aryl; heteroaryl; unsubstituted amino, and the amide thereof derived from a carboxylic acid of a substituent group; amino substituted with one substituent group, and the amide thereof derived from a carboxylic acid of a substituent group; amino substituted independently with one alkyl group and one substituent group; hydroxy, and the ester thereof derived from a carboxylic acid of a substituent group; ether having a substituent group; thiol, and the thiol ester thereof derived from a carboxylic acid of a substituent group; thioether having a substituent group, and the sulfoxide and sulfone derivative thereof; —$SO_3H$, the pharmaceutically-acceptable salts thereof, the ester thereof derived from an alcohol of a substituent group, the unsubstituted amide thereof, and the amide thereof substituted with one or two alkyl groups; —$CO_2H$, the pharmaceutically-acceptable salts thereof, the ester thereof derived from an alcohol of a substituent group, the unsubstituted amide thereof, and the amide thereof substituted with one or two alkyl groups; aldehyde; ketone having a substituent group; carbamate, unsubstituted or substituted with one or two alkyl groups; peptides having from about one to about 100 amino acid moieties; or the A and B moieties are covalently linked to form a ring having from 3 to about 7 atoms with from 0 to about 3 heteroatoms selected from the group consisting of nitrogen, sulfur, phosphorus and oxygen, the ring being unsubstituted or substituted with one or more of the above substituents of A; or the A and B moieties are replaced by an unsubstituted or substituted alkyl moiety attached to the geminal carbon (the carbon shown in structure (1) hereinabove) by a double bond.

Preferred A moieties are selected from:

(1) hydrogen;

(2) halogen; more preferred are F or Cl; most preferred is F;

(3) substituted and unsubstituted alkyl having the general structure:

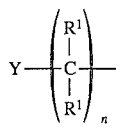

(2)

wherein n is an integer from 1 to about 10, preferably from 1 to about 5, more preferably n=1 or 2, and most preferably n=1; each $R^1$ is independently selected to achieve chemically-stable moieties from the group consisting of hydrogen, halogen, lower alkyl, unsubstituted amino or the amide thereof derived from a carboxylic acid of a lower alkyl group, amino substituted with one lower alkyl group or the amide thereof derived from a carboxylic acid of a lower alkyl group, amino substituted independently with two lower alkyl groups, hydroxy or the ester thereof derived from a carboxylic acid of a lower alkyl group, —$CO_2H$ or the pharmaceutically-acceptable salts thereof or the ester thereof derived from an alcohol of a lower alkyl group or the unsubstituted amide thereof or the amide thereof substituted with one or two lower alkyl groups, ether having a lower alkyl group, —$PO_3H_2$ or the pharmaceutically-acceptable salts thereof, and nitro, or two $R^1$'s on the same carbon atom are =O or =$NR^9$ (where R is lower alkyl or may be hydrogen when there is another nitrogen atom attached to the same as the =$NR^9$ moiety), or two $R^1$'s on adjacent carbon atom carbon atoms may be replaced by an additional bond between the carbon atoms; or an $R^1$ on the first carbon atom (from the right side of structure (2) hereinabove) and B (see structure (1) hereinabove) may be replaced by an additional bond; and Y is a substituent of alkyl as defined hereinbefore; (For the sake of chemical stability of the compounds of the present invention, $R^1$ cannot be such that there is a halogen and an oxygen or sulfur or nitrogen singly bonded to the same carbon atom or such that two of an oxygen or sulfur or nitrogen are singly bonded to the same carbon atom);

(4) Cycloalkyl having from about 4 to about 10 carbon atoms; more preferred are cycloalkyl having 5 or 6 carbon atoms;

(5) Heterocycle having 5 or 6 atoms in the ring; more preferred are heterocycles having one or two nitrogen atoms in the ring, more preferred still are heterocycles having one nitrogen atom in the ring; most preferred are unsubstituted or substituted piperidinyl, pyrrolidinyl, piperazinyl, morpholinyl;

(6) unsubstituted and substituted phenyl; naphthyl;

(7) unsubstituted and substituted 5 and 6 membered ring heteroaryls having one or two heteroatoms (especially nitrogen heteroatoms); most preferred is pyridinyl;

(8) amine-containing moiety having the general structure:

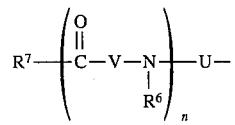

wherein m is an integer from 0 to about 10, preferably from 0 to about 5, more preferably 0 or 1, and most preferably m=0; $R^1$ and Y are as described hereinbefore; and $R^2$ is hydrogen, lower alkyl or acyl derived from a carboxylic acid of a lower alkyl;

(9) oxygen-containing moiety having the general structure:

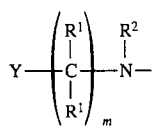

wherein m is an integer from 0 to about 10, preferably from 0 to about 5, more preferably 0 or 1, and most preferably m=0; and $R^1$ and Y are as described hereinbefore; and (10) sulfur-containing moiety having the general structure:

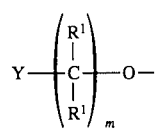

wherein m is an integer from 0 to about 10, preferably from 0 to about 5, more preferably 0 or 1, and most preferably m=0; and $R^1$ and Y are as described hereinbefore;

(11) peptide-containing moiety having the general structure:

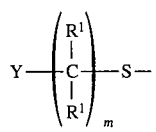

or

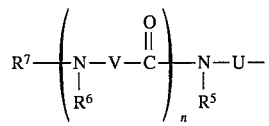

wherein n is an integer from 1 to about 100, preferably from 1 to about 6; $R^5$, each $R^6$ and $R^7$ are independently hydrogen or lower alkyl, preferably $R^5$, each $R^6$ and $R^7$ are hydrogen; U and each V are independently unsubstituted or substituted lower alkyl (substituted such that moiety is chemically-stable), or $R^5$ and U or each $R^6$ and V, together with the included nitrogen atom to which they are bound, may form a five- or six-membered ring which is unsubstituted or substituted; or U may be nil; preferably U and each V or rings in which they are incorporated are moieties found in naturally-occurring amino acid moieties, i.e. lysine, leucine, isoleucine, valine, phenylalanine, arginine, histidine, methionine, alanine, aspartic acid, threonine, proline, glycine, serine, tyrosine, tryptophan, glutamine and cysteine.

More preferred A moieties of the present invention are described and exemplified by the preferred methylene phosphonoalkylphosphinic acid compounds hereinafter.

B is a moiety selected from the group consisting of hydrogen; halogen; unsubstituted and substituted lower alkyl; unsubstituted and substituted cycloalkyl having from about 3 to about 7 atoms in the ring; unsubstituted and substituted heterocycle having from about 3 to about 7 atoms in the ring; Unsubstituted and substituted phenyl; hydroxy, and the ester thereof derived from a carboxylic acid of a lower alkyl group; thiol; unsubstituted amino, and the amide thereof derived from a carboxylic acid of a lower alkyl group; amino substituted with one lower alkyl group, and the amide thereof derived from a carboxylic acid of a lower alkyl group; amino substituted independently with two lower alkyl groups; —$CO_2H$, the pharmaceutically-acceptable salts thereof, the ester thereof derived from an alcohol of a lower alkyl group, the unsubstituted amide thereof, and the amide thereof substituted with one or two lower alkyl groups.

For the sake of chemical stability for the compounds of the present invention, it is preferred that the A and B moieties do not both have heteroatoms (N, O or S), or a heteroatom and a halogen, bonded to the methylene phosphonoalkylphosphinate moiety (i.e., the carbon atom geminally substituted with the phosphorous atoms). Thus, when the A moiety has an oxygen, sulfur, nitrogen, or halogen atom bonded to the phosphorous-substituted methylene carbon, then B is selected from hydrogen; unsubstituted or substituted lower alkyl, cycloalkyl, heterocycle (where a carbon atom of the heterocycle is bonded to the geminal carbon atoms), or phenyl; —CO₂H, the pharmaceutically-acceptable salts thereof, the ester thereof derived from an alcohol of a lower alkyl group, the unsubstituted amide thereof, and the amide thereof substituted with one or two lower alkyl groups.

Preferred B is selected from the group consisting of hydrogen, halogen, unsubstituted and substituted lower alkyl, unsubstituted and substituted phenyl, unsubstituted and substituted benzyl, hydroxy and the ester thereof derived from a carboxylic acid of a lower alkyl group, thiol, unsubstituted amino and the amide thereof derived from a carboxylic acid of a lower alkyl group, amino substituted with one lower alkyl group and the amide thereof derived from a carboxylic acid of a lower alkyl group, amino substituted independently with two lower alkyl groups, and —CO₂H and the pharmaceutically-acceptable salts thereof and the ester thereof derived from an alcohol of a lower alkyl group and the unsubstituted amide thereof or the amide thereof substituted with one or two lower alkyl groups.

More preferred B is selected from hydrogen, chloro, methyl, ethyl, hydroxy, thiol, unsubstituted amino, (N-methyl)amino, (N,N-dimethyl)amino, —CO₂H and the pharmaceutically-acceptable salts thereof, —CO₂CH₃, and —CONH₂. Most preferred B is selected from hydrogen, methyl, chloro, amino, and hydroxy; and especially hydrogen, or hydroxy, or amino, or thiol.

Preferred methylene phosphonoalkylphosphinic acids, and their pharmaceutically acceptable salts and esters, of the present invention are more particularly described as follows:

1. Alkyl- and cyclic-substituted methylene phosphonoalkylphosphinates:

Alkyl, cycloalkyl, aryl, heteroaryl and heterocyclic methylene phosphonoalkylphosphinic acids, and their pharmaceutically-acceptable salts and esters thereof, have the general structure:

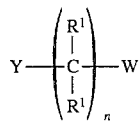

In this general structure, Y is preferably Y¹ or Z as hereinafter defined; n is an integer from 0 to about 10, more preferably from 0 to about 5. When Y is Y¹, n is more preferably from 1 to about 5. When Y is Z, n is more preferably 1 or 2, most preferably 1. Each R¹ moiety is independently selected as described hereinbefore, with preferred R¹ being selected from hydrogen, methyl, ethyl, hydroxy, unsubstituted amino, or two R¹'s on the same carbon atom are =O or =NR⁹ (where R⁹ is lower alkyl or may be hydrogen when there is another nitrogen atom attached to the same carbon atom as the =NR⁹ moiety), or two R¹'s on adjacent carbon atoms are replaced by an additional bond between the carbon atoms, or an R¹ on the first carbon atom (to the left of W in structure (3) hereinabove) and B (see structure (4) hereinbelow) may be replaced by an additional bond; and most preferred is all R¹ groups being hydrogen. W is the following structure:

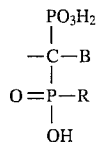

wherein the R and B moieties are as described hereinbefore.

When Y is Y¹, the Y¹ moiety is preferably selected from hydrogen, halogen, unsubstituted amino or the amide thereof derived from a carboxylic acid of a lower alkyl group, amino substituted with one lower alkyl group or the amide thereof derived from a carboxylic acid of a lower alkyl group, amino substituted independently with two lower alkyl groups, hydroxy or the ester thereof derived from a carboxylic acid of a lower alkyl group, —CO₂H or the pharmaceutically-acceptable salts thereof or the ester thereof derived from an alcohol of a lower alkyl group or the unsubstituted amide thereof or the amide thereof substituted with one or two lower alkyl groups.

More preferred Y¹ is hydrogen, halogen, unsubstituted amino or the amide thereof derived from a carboxylic acid of a lower alkyl group, amino substituted with one lower alkyl group, amino substituted independently with two lower alkyl groups, and hydroxy. Most preferred Y¹ is hydrogen, hydroxy, amino substituted with one methyl group, amino substituted with two methyl groups, and especially unsubstituted amino.

Representative examples of some alkyl methylene phosphonoalkylphosphinic acid compounds of the present invention include:

methylene phosphonomethylphosphinic acid:

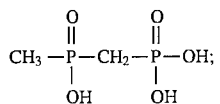

methylene phosphonobutylphosphinic acid:

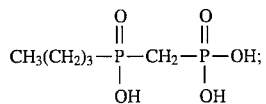

dichloromethylene phosphonomethylphosphinic acid; dichloromethylene phosphonoethylphosphinic acid, ethane phosphonomethylphosphinic acid; 1-hydroxy-ethane-1-phosphono-1-methyl-phosphinic acid:

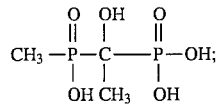

1-hydroxy-propane-1-phosphono-1-propylphosphinic acid;
2-amino-ethane-1-phosphono-1-methylphosphinic acid;
3-amino-propane-1-phosphono-1-methylphosphinic acid;
4-amino-butane-1-phosphono-1-methylphosphinic acid;
5-amino-pentane-1-phosphono-1-methylphosphinic acid;
6-amino-hexane-1-phosphono-1-methylphosphinic acid;
3-amino-1-hydroxy-propane-1-phosphono-1-methylphosphinic acid:

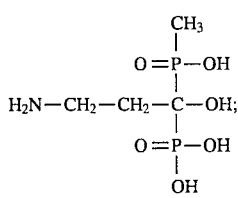

4-amino-1-hydroxy-butane-1-phosphono-1-methylphosphinic acid; 5-amino-1-hydroxy-pentane-1-phosphono-1-methylphosphinic acid; 6-amino-1-hydroxy-hexane-1-phosphono-1-methylphosphinic acid; 3-(N,N-dimethylamino)-1-hydroxy-propane-1-phosphono-1-methylphosphinic acid; 4-(N,N-dimethylamino)-1-hydroxy-butane-1-phosphono-1-methylphosphinic acid; 1,3-dihydroxy-propane-1-phosphono-1-butylphosphinic acid; 1,4-dihydroxy-butane-1-phosphono-1-propylphosphinic acid; 1,5-dihydroxy-pentane-1-phosphono-1-propylphosphinic acid; 2-amino-propane-1-phosphono-1-butylphosphinic acid; ethenylidene-1-phosphono-1-methylphosphinic acid:

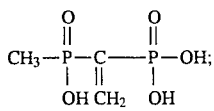

methylene phosphono(1'-but-3'-enyl)phosphinic acid:

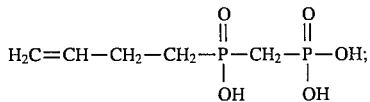

methylene phosphono(trifluoromethyl)phosphinic acid:

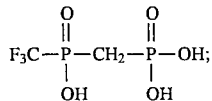

methylene phosphono(1'-(2'-phenyl)ethyl)phosphinic acid; methylene phosphono(1'-(2'-phenyl)butyl)phosphinic acid; and the pharmaceutically-acceptable salts and esters thereof.

When Y is Z, the Z moiety is selected from the group consisting of unsubstituted or substituted cycloalkyl, heterocycle, aryl and heteroaryl; with preferred Z being selected from five-membered ring heterocycles and heteroaryls having one heteroatom, five-membered ring heterocycles and heteroaryls having two heteroatoms, unsubstituted or substituted phenyl, six-membered ring heterocycles and heteroaryls having one heteroatom, and six-membered ring heterocycles and heteroaryls having two heteroatoms; and preferably all the heteroatoms in the ring are nitrogen. More preferred Z is pyrrolidinyl, pyrrolyl, pyridinyl, piperidinyl, piperidinylidene, pyridazinyl, pyrimidinyl, pyrazinyl, and morpholinyl. Most preferred is pyrimidinyl, and especially piperidinyl and pyridinyl.

The Z moiety may be unsubstituted or substituted. Preferred is the Z moiety being unsubstituted or substituted on the carbon atoms of the ring with one or more substituents selected from the group consisting of halogen; lower alkyl; unsubstituted amino, and the amide thereof derived from a carboxylic acid of a lower alkyl group; amino substituted with one lower alkyl group, and the amide thereof derived from a carboxylic acid of a lower alkyl group; amino substituted independently with two lower alkyl groups; hydroxy, or the ester thereof derived from a carboxylic acid of a lower alkyl group; ether having a lower alkyl group; —CO$_2$H, the pharmaceutically-acceptable salts thereof, the ester thereof derived from an alcohol of a lower alkyl group, the unsubstituted amide thereof, and the amide thereof substituted with one or two lower alkyl groups; nitro; and combinations thereof. Non-aromatic nitrogen atoms in the Z heterocycle moiety may be unsubstituted or substituted with a lower alkyl group. More preferred is the Z moiety being unsubstituted or substituted on the carbon atoms of the ring with one or more substituents selected from the group consisting of halogen, lower alkyl, unsubstituted amino and the acetyl amide thereof, amino substituted with one methyl group and the acetyl amide thereof, amino substituted with two methyl groups, hydroxy and the acetyl ester thereof, methyl ether, ethyl ether, —CO$_2$H and the pharmaceutically-acceptable salts thereof, —CO$_2$CH$_3$, —CO$_2$C$_2$H$_5$, —CONH$_2$, —CONHCH$_3$, —CON(CH$_3$)$_2$, and nitro. More preferred is the Z moiety being unsubstituted, or mono-, di-, or tri-substituted independently with the preceding substituents. Most preferred is the Z moiety being unsubstituted, or mono-substituted with a substituent selected from the group consisting of methyl, ethyl, fluoro, chloro, bromo, trifluoromethyl, hydroxy, (N-methyl)amino, (N,N-dimethyl)amino, methyl ether, —CO$_2$H and the pharmaceutically-acceptable salts thereof, —CO$_2$CH$_3$, —CONH$_2$, and especially unsubstituted amino.

Preferred compounds of the present invention of this type are substituted ethane phosphonoalkylphosphinic acids, and the pharmaceutically-acceptable salts and esters thereof, having the general structure:

wherein the Z and W moieties, as well as the substituents on the Z moiety, are as described hereinbefore. Particularly preferred are the pyridinyl ethane phosphonoalkylphosphinic acids, salts and esters having the general structure:

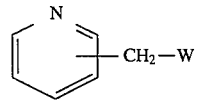

and the piperidinyl ethane phosphonoalkylphosphinic acids, salts and esters having the general structure:

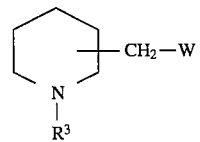

wherein the W moiety is as described hereinbefore; the R$^3$ moiety is selected from lower alkyl (preferably methyl, ethyl, or propyl) and especially hydrogen; and the pyridinyl and piperidinyl rings may be unsubstituted or substituted as described hereinbefore.

Representative examples of this type of methylene phosphonoalkylphosphinic acid compounds of the present invention include: phenyl-methane phosphonomethylphosphinic acid; 2-(phenyl)-1-hydroxy-ethane-1-phosphono-1-methylphosphinic acid; 2-(p-aminophenyl)-1-hydroxyethane-1-phosphono-1-methylphosphinic acid; (2'-pyridinyl)-methane phosphonobutylphosphinic acid; (3'-piperidinyl)-methane phosphonoethylphosphinic acid; 2-(2'-pyridinyl)-ethane-1-phosphono-1-methyl phosphinic acid; 2-(2'-pyridinyl)-ethane-1-phosphono-1-butylphosphinic acid:

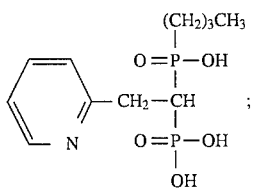

2-(2'-pyridinyl)-1-hydroxy-ethane-1-phosphono-1-methylphosphinic acid; 2-(3'-pyridinyl)-ethane-1-phosphono-1-methylphosphinic acid; 2-(3'-pyridinyl)-1-hydroxy-ethane-1-phosphono-1-methylphosphinic acid:

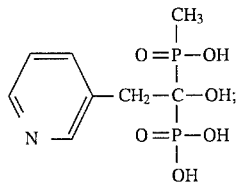

2-(4'-pyridinyl)-ethane-1-phosphono-1-methylphosphinic acid; 2- (4'-pyridinyl)-1-hydroxyethane-1-phosphono-1-methylphosphinic acid; 3-(2'-pyridinyl)-propane-1-phosphono-1-butylphosphinic acid; 3-(2'-pyridinyl)-propane-2,2-phosphonomethylphosphinic acid; 2-(2'-piperidinyl)-1-hydroxy-ethane-1-phosphono-1-methylphosphinic acid; 2-(3'-piperidinyl)-1-hydroxy-ethane-1-phosphono-1-methylphosphinic acid:

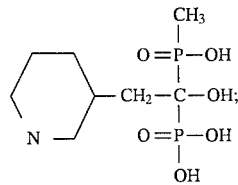

2-(4'-piperidinyl)-1-hydroxy-ethane-1-phosphono-1-methylphosphinic acid; 2-(2'-pyrrolidinyl)-1-hydroxy-ethane-1-phosphono-1-methylphosphinic acid; 2-(3'-pyrrolyl)-1-hydroxy-ethane-1-phosphono-1-methylphosphinic acid; 2-(2'-piperidinyl)-ethane-1-phosphono-1-methylphosphinic acid; 2-(3'-piperidinyl)-ethane-1-phosphono-1-methylphosphinic acid; 2-(4'-piperidinyl)-ethane-1-phosphono-1-methylphosphinic acid; 2-(3'-pyridazinyl)-ethane-1-phosphono-1-propylphosphinic acid; 2-(2'-pyrimidinyl)-ethane-1-phosphono-1-ethylphosphinic acid; 2-(2'-pyrazinyl)-ethane-1-phosphono-1-butylphosphinic acid; 5-(2'-pyridinyl)-pentane-1-phosphono-1-methylphosphinic acid; 4-(2'-piperidinyl)-1-hydroxy-butane-1-phosphono-1-methylphosphinic acid.

2. Hetero-substituted methylene phosphonoalkylphosphinates

Hetero-substituted methylene phosphonoalkylphosphinic acids, and the pharmaceutically-acceptable salts and esters thereof, have the general structure:

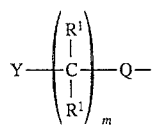

In this general structure, Y is as described hereinbefore, and m is an integer from 0 to about 10, preferably from 0 to about 5. Q is a heteroatom selected from oxygen, sulfur and $NR^2$; with $R^2$ being lower alkyl, acyl derived from a carboxylic acid of a lower alkyl group, and especially hydrogen, or $R^2$ is replaced by a second bond between the nitrogen which it is on and an adjacent atom capable of accepting a second bond. The $R^1$ and W moieties are as described hereinbefore, except that preferred B is selected from hydrogen; unsubstituted and substituted lower alkyl, phenyl, benzyl; and $—CO_2H$ or the pharmaceutically-acceptable salts thereof or the ester thereof derived from an alcohol having a lower alkyl group or the substituted amide thereof or the amide thereof substituted with one or two lower alkyl groups.

Representative examples of compounds of the present invention when Y is $Y^1$ include the following: amino methylene phosphonoethylphosphinic acid; N-(1-(5-amino-2-methyl-1-oxo)-pentyl)-amino methylene phosphonomethylphosphinic acid:

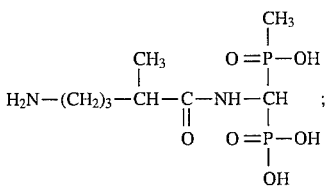

When Y is Z, m is more preferably from 0 to about 2; especially preferred is m being 0 or 1; most preferred is m=0.

Preferred compounds of the present invention of this type are substituted aminomethylene phosphonoalkylphosphinic acids, and the pharmaceutically-acceptable salts and esters thereof, having the general structure:

wherein the Z, W and $R^2$ moieties, as well as the substituents on the Z moiety, are as described hereinbefore. Particularly preferred is the pyridinyl aminomethylene phosphonoalkylphosphinic acids, salts and esters having the general structure:

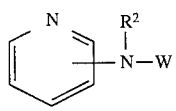

wherein the W and $R^2$ groups are as described hereinbefore; and the pyridinyl ring may be unsubstituted or substituted as described hereinbefore. Also particularly preferred is the piperidinyl aminomethylene phosphonoalkylphosphinic acids, salts and esters having the general structure:

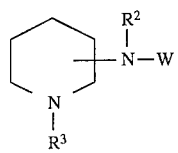

wherein the W, $R^2$ and $R^3$ groups are as described hereinbefore; the piperidinyl ring may be unsubstituted or substituted as described hereinbefore. Preferably the nitrogen is bonded to the ring at a carbon not bonded directly to the ring's nitrogen atom (the 3, 4 or 5 position). Further, when the nitrogen atoms are both bonded to the same carbon atom in the piperidinyl ring, one with a double bond, these compounds have one or both of the following piperidinylidene structures:

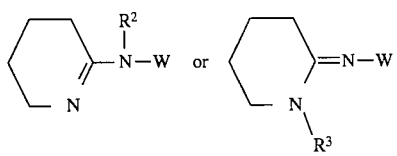 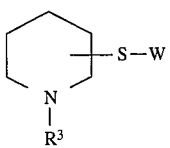

In these piperidinylidene compounds wherein $R^2$ and $R^3$ are both hydrogen (which is preferred), these compounds are probably an equilibrium mixture of both the above piperidinylidene structures.

Further preferred compounds of this type are substituted oxomethylene phosphonoalkylphosphinic acids, and the pharmaceutically-acceptable salts and esters thereof, having the general structure:

Z—O—W wherein the Z and W groups, as well as the substituents on the Z moiety, are as described hereinbefore. Particularly preferred is the pyridinyl oxomethylene phosphonoalkylphosphinic acids, salts and esters having the general structure:

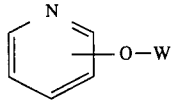

wherein the W group is as described hereinbefore, and the pyridinyl ring may be unsubstituted or substituted as described hereinbefore. Also particularly preferred is the piperidinyl oxomethylene phosphonoalkylphosphinic acids, salts and esters having the general structure:

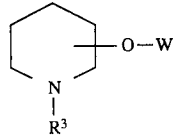

wherein the W and $R^3$ groups are as described hereinbefore; the piperidinyl ring may be unsubstituted or substituted as described hereinbefore; and wherein further the oxygen is bonded to the ring at a carbon atom not bonded directly to the ring's nitrogen atom (the 3, 4 or 5 position).

Preferred compounds of this type also include substituted thiomethylene phosphonoalkylphosphinic acids, and the pharmaceutically-acceptable salts and esters thereof, having the general structure:

Z—S—W wherein the Z and W groups, as well as the substituents on the Z moiety, are as described hereinbefore. Particularly preferred is the pyridinyl thiomethylene phosphonoalkylphosphinic acids, salts and esters having the general structure:

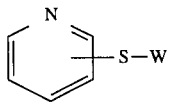

wherein the W group is as described hereinbefore, and the pyridinyl ring may be unsubstituted or substituted as described hereinbefore. Also particularly preferred is the piperidinyl thiomethylene phosphonoalkylphosphinic acids, salts and esters having the general structure:

wherein the W and $R^3$ groups are as described hereinbefore; the piperidinyl ring may be unsubstituted or substituted as described hereinbefore; and wherein further the sulfur is bonded to the ring at a carbon atom not bonded directly to the ring's nitrogen atom (the 3, 4 or 5 position).

Representative examples of these types of methylene phosphonoalkylphosphinic acid compounds of the present invention include: N-(phenyl)-aminomethane phosphonomethylphosphinic acid; N-(phenyl)-aminomethane phosphono(trifluoromethyl)phosphinic acid; N-(2'-pyridinyl)-aminomethane phosphonomethylphosphinic acid:

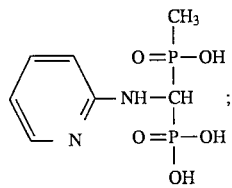

N-(3'-pyridinyl)-aminomethane phosphonomethylphosphinic acid; N-(4'-pyridinyl)-aminomethane phosphonomethylphosphinic acid; N-(2'-(3'-methyl)-pyridinyl)-aminomethane phosphonomethylphosphinic acid:

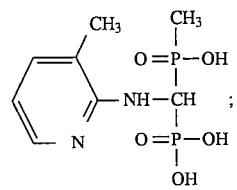

N-(2'-(3'-methyl)-pyridinyl)-aminomethane phosphonobutylphosphinic acid:

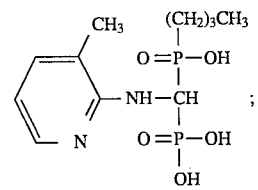

N-(2'-(4'-methyl)-pyridinyl)-aminomethane phosphonomethylphosphinic acid; N-(2'-(5'-methyl)-pyridinyl)-aminomethane phosphonomethylphosphinic acid:

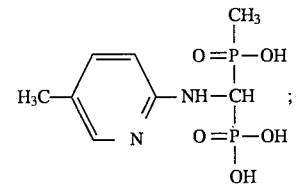

N-(2'-(6'-methyl)-pyridinyl)-aminomethane phosphonomethylphosphinic acid; 3-(N-(2'-pyridinyl))-amino-propane-1-phosphono-1-propylphosphinic acid; N-(2'-piperidinylidene)-aminomethane phosphonomethylphosphinic acid; N-(3'-piperidinyl)-aminomethane phosphonomethylphosphinic acid; N-(4'-piperidinyl)-aminomethane phosphonomethylphosphinic acid; N-(2'-(3'-methyl)-piperidinylidene)-aminoethane phosphonomethylphosphinic acid:

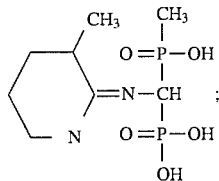

N-(2'-(3'-methyl)-piperidinylidene)-aminomethane phosphono trifluoromethyl phosphinic acid:

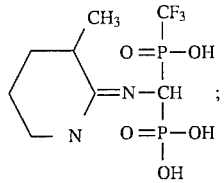

N-(2'-(3'-methyl)-piperidinylidene)-aminomethane phosphonobutylphosphinic acid; N-(2'-(4'-methyl)-piperidinylidene)-aminomethane phosphonomethylphosphinic acid; N-(2'-(5'-methyl)-piperidinylidene)-aminoethane phosphonomethylphosphinic acid:

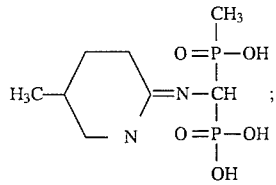

N-(2'-(6'-methyl)-piperidinylidene)-aminomethane phosphonomethylphosphinic acid; N-(3'-pyrrolidinyl)-aminomethane phosphonoethylphosphinic acid; N-(2'-pyrrolyl)-aminomethane phosphonobutylphosphinic acid; N-(2'-pyrimidinyl)-aminomethane phosphonomethylphosphinic acid; S-(phenyl)-thiomethane phosphonomethylphosphinic acid; S-(2'-pyridinyl)-thiomethane phosphonomethylphosphinic acid:

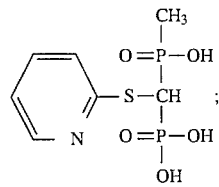

S-(3'-pyridinyl)-thiomethane phosphonomethylphosphinic acid; S-(4¹-chlorophenyl)-thiomethane phosphonomethylphosphinic acid:

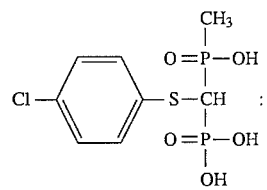

S-(4'-pyridinyl)-thiomethane phosphonomethylphosphinic acid; S-(3'-piperidinyl)-thiomethane phosphonomethylphosphinic acid; S-(4'-piperidinyl)-thiomethane phosphonomethylphosphinic acid; S-(2'-pyrrolyl)-thiomethane phosphonomethylphosphinic acid; S-(3'-pyrrolyl)-thiomethane phosphonomethylphosphinic acid; S-(3'-pyrrolidinyl)-thiomethane phosphonomethylphosphinic acid; S-(2'-pyrimidinyl)-thiomethane phosphonomethylphosphinic acid; 1-(S-(2'-pyridinyl))-thioethane-1-phosphono-1-methylphosphinic acid; 2-(S-(2'-pyridinyl))-thioethane-1-phosphono-1-methylphosphinic acid; O-(phenyl)-oxomethane phosphonomethylphosphinic acid; O-(2'-pyridinyl)-oxomethane phosphonomethylphosphinic acid; O-(3'-pyridinyl)-oxomethane phosphonomethylphosphinic acid; O-(4'-pyridinyl)-oxomethane phosphonomethylphosphinic acid; O-(3'-piperidinyl)-oxomethane phosphonomethylphosphinic acid; O-(4'-piperidinyl)-oxomethane phosphonomethylphosphinic acid; O-(2'-pyrrolyl)-oxomethane phosphonomethylphosphinic acid; O-(3'-pyrrolyl)-oxomethane phosphonomethylphosphinic acid; O-(3'-pyrrolidinyl)-oxomethane phosphonomethylphosphinic acid; O-(2'-pyrimidinyl)-oxomethane phosphonomethylphosphinic acid; 1-(O-(2'-pyridinyl))-oxoethane-1-phosphono-1-methylphosphinic acid; 2-(O-(2'-pyridinyl))-oxoethane-1-phosphono-1-methylphosphinic acid; and the pharmaceutically-acceptable salts and esters thereof.

3. Cyclic methylene phosphonoalkylphosphinates

Cyclic methylene phosphonoalkylphosphinic acids, and the pharmaceutically-acceptable salts and esters thereof, have the general structure:

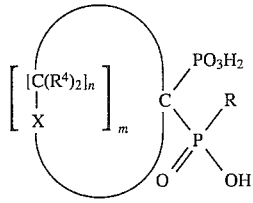

In this general structure, m is an integer from 1 to about 2, preferably 1, and each n is independently an integer from about 1 to about 6, and the sum of all n's is from about 2 to about 6. Preferably the sum of all n's plus the number of X's which are not nil is 4 or 5, and most preferably 4. Each —X— is independently selected from the group consisting of —O—, —S—,

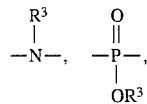

and nil; preferably from —O—, —S—,

and nil; more preferably from

and nil; where $R^3$ is hydrogen or unsubstituted lower alkyl, preferably hydrogen. The R moiety is as described hereinbefore. Each $R^4$ group is selected independently to form a chemically-stable compound from hydrogen; halogen; lower alkyl; phenyl; benzyl; unsubstituted amino, or the amide thereof derived from a carboxylic acid of a lower alkyl group; amino substituted with one lower alkyl group, or the amide thereof derived from a carboxylic acid of a lower alkyl group; amino substituted independently with two lower alkyl groups; hydroxy, or the ester thereof derived from a carboxylic acid of a lower alkyl group; ether having a lower alkyl group; —$CO_2H$, the pharmaceutically-acceptable salts thereof, the ester thereof derived from an alcohol of a lower alkyl group, the unsubstituted amide thereof, or the amide thereof substituted with one or two lower alkyl groups; and nitro. Two $R^4$ groups on adjacent carbon atoms may be replaced by an additional bond between the carbon atoms. Two $R^4$ groups on adjacent carbon atoms may form a 5- or preferably 6- membered cycloalkyl, heterocyclic, aryl, or heteroaryl ring fused with the methylene phosphonoalkylphosphinate-containing ring.

For the sake of chemical stability of the compounds of the present invention, $R^4$ cannot be such that there is a halogen and an oxygen or sulfur or nitrogen or phosphorus singly bonded to the same carbon atom or such that two of oxygen or sulfur or nitrogen or phosphorus are singly bonded to the same carbon atom.

More preferred $R^4$ groups are hydrogen; alkyl having from 1 to about 3 carbon atoms; unsubstituted amino; amino substituted with one alkyl group having from 1 to about 3 carbon atoms; amino substituted with two alkyl groups having from 1 to about 3 carbon atoms; hydroxy; two $R^4$ groups on adjacent carbon atoms being replaced by an additional bond; two $R^4$ groups on adjacent carbon atoms forming a fused phenyl ring; two $R^4$ groups on adjacent carbon atoms forming a fused cyclohexyl ring; two $R^4$ groups on adjacent carbon atoms forming a saturated 6-membered ring containing one nitrogen atom; and combinations thereof.

In the above cyclic methylene phosphonoalkylphosphinate structure, preferred are structures where the sum of carbon atoms and heteroatoms making up the cyclic ring is 4 or 5, with none, one or two heteroatoms. Nitrogen heteroatoms are preferred. Most preferred are structures with no heteroatoms, or one nitrogen heteroatom.

Preferred cyclic methylene phosphonoalkylphosphinic acids, salts, and esters are:

(a) unsubstituted or substituted cyclopropane-1-phosphono-1-alkylphosphinates having the general structure:

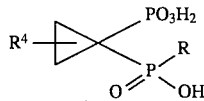

(b) unsubstituted or substituted cyclobutane-1-phosphono-1-alkylphosphinates having the general structure:

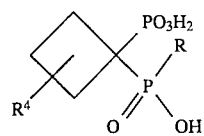

(c) unsubstituted or substituted cyclopentane-1-phosphono-1-alkylphosphinates having the general structure:

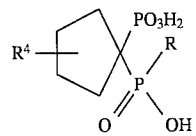

(d) unsubstituted or substituted cyclopentene-1-phosphono-1-alkylphosphinates having the general structure:

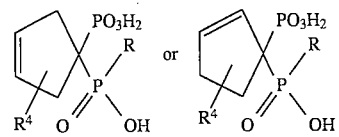

(e) unsubstituted or substituted cyclohexane-1-phosphono-1-alkylphosphinates having the general structure:

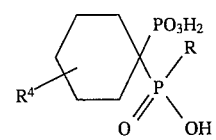

(f) unsubstituted or substituted cyclohexene-1-phosphono-1-alkylphosphinates having the general structures:

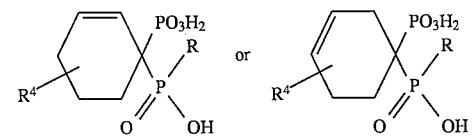

(g) unsubstituted or substituted cycloheptane-1-phosphono-1-alkylphosphinates having the general structure:

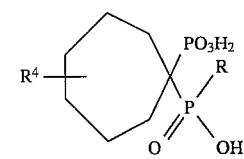

(h) unsubstituted or substituted indan-2,2-phosphonoalkylphosphinates having the general structure:

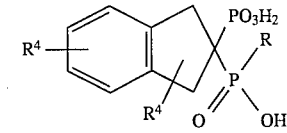

(i) unsubstituted or substituted hexahydroindan-2,2-phosphonoalkylphosphinates having the general structure:

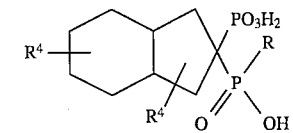

(j) unsubstituted or substituted octahydropyrindine-6,6-phosphonoalkylphosphinates having the general structures:

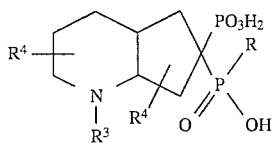

or

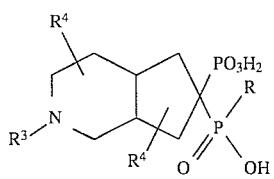

(k) unsubstituted or substituted pyrrolidine-2-phosphono-2-alkylphosphinates and pyrrolidine-3-phosphono-3-alkylphosphinates having the general structures:

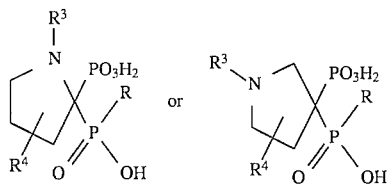

(l) unsubstituted or substituted piperidine-2-phosphono-2-alkylphosphinates, piperidine-3-phosphono-3-alkylphosphinates and piperidine-4-phosphono-4-alkylphosphinates having the general structures:

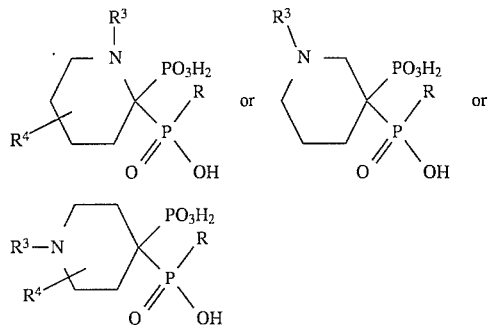

(m) unsubstituted or substituted octahydro[2,3-b]- and [2,3-c]pyrrolopyridine-5-phosphono-5-alkylphosphinates having the general structures:

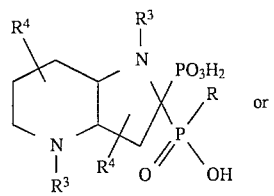

-continued

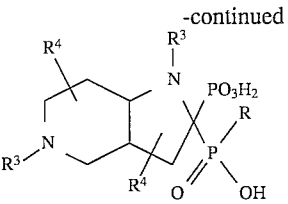

(n) unsubstituted or substituted octahydro[2,3-b]- and [2,3-c]furanpyridine-5-phosphono-5-alkylphosphinates having the general structures:

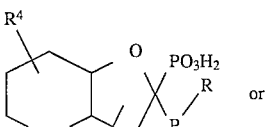

or

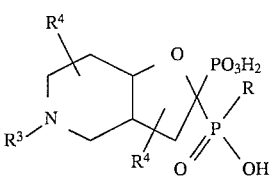

The R, $R^3$ and $R^4$ moieties in these general structures are as described hereinbefore. More preferred in these general structures is one $R^4$ group being selected from hydrogen, hydroxy, unsubstituted amino, methyl, ethyl, or chloro, and the other $R^4$ groups being hydrogen. Most preferred is all $R^4$ groups being hydrogen.

Representative examples of cyclic methylene phosphonoalkylphosphinic acid compounds of the present invention include: cyclopentane-1-phosphono-1-methylphosphinic acid; cyclopent-2-ene-1-phosphono-1-butylphosphinic acid; cyclopent-3-ene-1-phosphono-1-methylphosphinic acid; cyclohexane-1-phosphono-1-methylphosphinic acid; cyclohex-2-ene-1-phosphono-1-methylphosphinic acid; cyclohex-3-ene-1-phosphono-1-methylphosphinic acid; indan-2,2-phosphonomethylphosphinic acid; hexahydroindan-2,2-phosphonomethylphosphinic acid; 1-octahydropyrindine-6,6-phosphonomethylphosphinic acid:

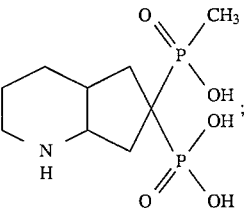

1-octahydropyrindine-6,6-phosphonobutylphosphinic acid; and the pharmaceutically-acceptable salts and esters thereof.

The term "pharmaceutically-acceptable salts and esters", as used herein, means hydrolyzable esters and salts of the methylene phosphonoalkylphosphinate compounds which have the same general pharmacological properties as the acid form from which they are derived, and which are acceptable from a toxicity viewpoint. Pharmaceutically-acceptable salts include alkali metals (e.g., sodium and potassium), alkaline earth metals (e.g., calcium and magnesium), non-toxic heavy metals (e.g., stannous and indium), and ammonium and low molecular weight substituted ammonium (e.g., mono-, di- and triethanolamine) salts. Preferred compounds are the sodium, potassium, and ammonium salts. Pharmaceutically-acceptable esters include unsubstituted and substituted alkyl, aryl and phosphoryl esters. Nonlimiting examples of pharmaceutically-acceptable esters may include isopropyl, tertiarybutyl, 2-chloroethyl, 2,2,2-trichloroethyl, 2,2,2-trifluoroethyl, p-toluenesulfonylethyl, glycyl, sarcosyl, benzyl, phenyl, 1,2-hexanoylglyceryl, p-nitrophenyl, 2,2 dimethyl-1,3-dioxolene-4-methyl, isopentenyl, o-carbomethoxyphenyl, piraloyloxymethylsalicylyl, diethylamidophosphoryl, pivaloyloxymethyl, acyloxymethyl, propionyloxymethyl, isobutyryloxymethyl, dodecyl, octadecyl, and isopropyloxymethyl.

Certain of the compounds of the present invention demonstrate significantly better bone anti-resorptive activity than art-known diphosphonate compounds such as ethane-1-hydroxy-1,1-diphosphonic acid ("EHDP"; disclosed in U.S. Pat. No. 3,683,080, to Francis, issued Aug. 8, 1972). Typically, however, the compounds of the present invention are less potent bone resorption-inhibiting agents than the analogous diphosphonate compounds. Generally, the compounds of the present invention appear to have a lowest effective dose ("LED"; as described more fully hereinafter) which is about 10–100 times higher (i.e., need a higher dose to get a significant effect) than the analogous diphosphonate compounds. Although less than that of analogous diphosphonate compounds, the relatively high potency of the methylene phosphonoalkylphosphinate compounds was unexpected. Phosphinate compounds have been reported to have little bone uptake. (See Surh, Spencer, Spitanagle, Hosain & Lejczak, "Technetium-99m-Labeled Phosphonic Acid Analog of Serine: Bone Uptake", *Journal of Nuclear Medicine*, Vol. 27, No. 6 (June 1986), pp. 847–849)

While generally being a less potent anti-resorptive agent by about one-two orders of magnitude, the dosing levels at which a compound of the present invention demonstrates toxicity is generally greater than two orders of magnitude higher than the toxic dose for an analogous diphosphonate compound. The net result is that the compounds of the present invention generally demonstrate greater therapeutic indices than analogous diphosphonate compounds. Thus, while generally having to be dosed at a somewhat higher level than analogous diphosphonates, the compounds of the present invention demonstrate a larger margin of safety for dosing.

An additional benefit of the compounds of the present invention is their general lower affinity for bone. Therefore, the compounds of the present invention are expected to inhibit bone mineralization either very little or not at all. This property further enhances the therapeutic indices of the compounds of the present invention. It provides an advantage in treating diseases such as osteoporosis and Paget's disease by permitting mineralization of bone while preventing resorption of bone.

Furthermore, the compounds of the present invention are generally more lipophilic and are expected to be more readily absorbed after oral administration than diphosphonates. The methylene phosphonoalkylphosphinate compounds may also be generally absorbed at a more consistent level than diphosphonates.

In order to determine and assess pharmacological activity, testing of the methylene phosphonoalkylphosphinate compounds in animals is carried out using various assays known to those skilled in the art. Thus, the bone activity of the compounds of the present invention may be conveniently demonstrated using an assay designed to test the ability of compounds to inhibit the resorption of bone, which bone resorption is characteristic of abnormal calcium and phosphate metabolism. Examples of such known tests include the thyroparathyroidectomized ("TPTX") rat model and the Schenk model. Another useful art-known test is the adjuvant arthritis test which may be used for assessing bone anti-resorptive activity in a chronic, rather than acute, model. These and other appropriate tests for pharmacological activity are disclosed and/or referred to in Shinoda et al., *Calcified Tissue International*, 35, pp 87–99 (1983); Schenk et al., *Calcified Tissue Research*, 11, pp 196–214 (1973); Russell et al., *Calcified Tissued Research*, 6, pp 183–196 (1970); Muhlbauer and Fleisch, *Mineral Electrolyte Metab.*, 5, pp 296–303 (1981); Nancollas et al., *Oral Biol.*, 15, 731 (1970); U.S. Pat. No. 3,962,432, to Schmidt-Dunker, issued Jun. 8, 1976; U.S. Pat. No. 4,134,969, to Schmidt-Dunker, issued Jan. 16, 1979; U.S. Pat. No. 3,683,080, to Francis, issued Aug. 8, 1972; the disclosures of all these articles and patents being incorporated herein by reference in their entirety. Certain of these tests for pharmacological activity are also described in more detail in the examples provided hereinafter.

It is preferred that the compounds of the present invention have an LED, as determined by the TPTX rat model, that is less than or equal to about 10 mg/kg. Therefore, the preferred compounds of the present invention are analogs (preferably the lower alkylphosphinate analog; more preferably the methyl, ethyl, propyl, or butyl phosphinate analog; and most preferably the methyl phosphinate analog) of diphosphonate compounds having a TPTX rat model LED that is less than or equal to about 1 mg/kg, most preferably less than or equal to about 0.1 mg/kg. Such diphosphonate compounds are disclosed in the following references which are hereby incorporated in their entirety herein by reference: U.S. Pat. Nos. 3,683,080 issued to Francis on Aug. 8, 1972; 3,846,420 issued to Wollmann, Ploger & Worms on Nov. 5, 1974; 3,899,496 issued to Schindler & Ploger on Aug. 12, 1975; 3,957,160 issued to Ploger & Worms on May 18, 1976; 3,962,432 issued to Schmidt-Dunker on Jun. 8, 1976; 3,979,385 issued to Wollmann, Ploger & Worms on Sep. 7, 1976; 3,988,443 issued to Ploger, Schmidt-Dunker & Gloxhuber on Oct. 26, 1976; 4,100,167 issued to Selvarajan & Ballweber on Jul. 11, 1978; 4,113,861 issued to Fleisch & Felix on Sep. 12, 1978; 4,134,969 issued to Schmidt-Dunker on Jan. 16, 1979; 4,239,695 issued to Chai & Muggee on Dec. 16, 1980; 4,267,108 issued to Blum, Hempel & Worms on May 12, 1981; 4,304,734 issued to Jary, Rihakova & Zobacova on Dec. 8, 1981; 4,407,761 issued to Blum & Worms on Oct. 4, 1983; 4,447,256 issued to Suzuki, Fujikawa, Yamamoto, Mizutani, Ohya, Ikai & Oguchi on May 8, 1984; 4,473,560 issued to Biere, Rufer & Boettcher on Sep. 25, 1984; 4,503,049 issued to Biere, Rufer & Boettcher on Mar. 5, 1985; 4,578,376 issued to Rosini on March 25, 1986; and 4,621,077 issued to Rosini & Staibano on Nov. 4, 1986; U.S. patent applications Ser. Nos. 684,544 of Benedict & Johnson filed Dec. 21, 1984; and 808,584 of Benedict & Perkins filed Dec. 13, 1985; European Patent Applications Nos. 0,100,718 of Sanofi SA published Feb. 15, 1984; 0,151,072 of Sanofi SA published Aug. 7, 1985; 170,228 of Boehringer Mannheim GmbH published Feb. 5, 1986; 0,197,478 of Boehringer Mannheim GmbH published Oct. 15, 1986; German Patent Applications Nos. 2,831,578 of Nissan Chemical Industries, Ltd. published Feb. 1, 1979; and 3,334,211 of Henkel KGaA published Apr. 4, 1985; UK Patent Application No. 2,004,888 of Nissan Chemical Industries, Ltd. published Apr. 11, 1979; Japanese Patent Application No. 55-98193 of Nissan Kagaku Kogyo KK published Jul. 25, 1980; Ploger, W., N. Schindler, K. Wollmann & K. H. Worms, "Preparation of 1-aminoalkane-1,1-diphosphonic Acids", *Z. Anorg. Allg. Chem.*, Volume 389 (1972), pp. 119–128; Worms, K. H., H. Blum & H. U. Hempel, "Synthesis of 2- or 3-substituted Alkanediphosphonic Acids", *Z. Anorg. Allg. Chem.*, Volume 457 (1979), pp. 214–218; Maier, L., "Amino-methylenediphosphinates and -diphosphonates", *Phosphorus and Sulfur*, Volume 11 (1981), pp. 311–322; Worms, K. H., & H. Blum, "Geminal Diphosphonic Acids Containing Amidino Groups", *Liebigs Ann. Chem.*, 1982, pp. 275–281.

The compounds of the present invention may be made by a variety of methods, especially by modifying the methods used to prepare analogous diphosphonate compounds which are disclosed in the references regarding diphosphonate compounds incorporated hereinbefore.

In addition, the syntheses of certain methylene phosphonoalkylphosphinate compounds are known and are disclosed in the references which disclose such compounds and which have been incorporated by reference hereinbefore. Representative procedures for synthesizing compounds of the present invention are provided in the examples hereinafter. Based on the teachings of these examples and of the above-mentioned references, the synthesis of the methylene phosphonoalkylphosphinate compounds of the present invention is within the purview of a skilled chemist.

Compounds of the present invention may comprise from about 0.1% to about 99.9% by weight of the pharmaceutical compositions of the present invention. Preferably the compounds of the present invention comprise from about 20% to about 95% by weight of the pharmaceutical compositions of the present invention, and most preferably from about 50% to about 90%.

Pharmaceutically-acceptable Carrier

In addition to the methylene phosphonoalkylphosphinate compounds as described hereinbefore, the pharmaceutical compositions of the present invention essentially contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical composition are capable of being commingled with the methyl phosphonoalkylphosphinate compounds, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin, talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; and phosphate buffer solutions, wetting agents and lubricants such as sodium lauryl sulfate, coloring agents, flavoring agents, preservatives, as well as other non-toxic compatible substances used in pharmaceutical formulations.

Other compatible pharmaceutical additives and actives may be included in the pharmaceutically-acceptable carrier for use in the compositions of the present invention.

The choice of a pharmaceutically-acceptable carrier to be used in conjunction with the methylene phosphonoalkylphosphinate compound is determined by the way the methylene phosphonoalkylphosphinate compound is to be administered. If the compound is to be injected, the preferred pharmaceutical carrier is sterile water, physiological saline, or mixtures thereof, the pH of which has been adjusted to about 7.4. Suitable pharmaceutically-acceptable carriers for topical application include those suited for use in creams, gels, tapes and the like.

The preferred mode of administering a methylene phosphonoalkylphosphinate compound is orally. The preferred unit dosage form is therefore tablets, capsules, suspensions, solutions, and the like, comprising a safe and effective amount of the methylene phosphonoalkylphosphinate compound of the present invention. Preferably, the compositions comprise from about 1 mg P to about 600 mg P of a methylene phosphonoalkylphosphinate compound of the present invention. Pharmaceutically-acceptable carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art.

The term "mg P", as used herein, means the weight of the phosphorous atoms present in an amount of a methylene phosphonoalkylphosphinic acid compound of the present invention. This unit is used to standardize the amount of the methylene phosphonoalkylphosphinic acid compounds of the present invention to be used in the pharmaceutical compositions and methods of the present inventions. For example, 2-(2'-piperidinyl)-ethane-1-phosphono-1-methylphosphinic acid has a molecular weight of 271 g/mole, of which 22.9% (62 g/mole) is due to the two phosphorous atoms present in this molecule. One milligram of this compound is therefore calculated to have 0.229 mg P (1 mg×22.9%). Thus, to prepare a pharmaceutical composition containing 0.229 mg P of this compound, the composition should contain 1 mg of the compound; and to dose 0.229 mg P/kg of this compound to a 50 kg patient, the patient would be dosed with 50 mg of this compound.

The pharmaceutically-acceptable carrier employed in conjunction with the methylene phosphonoalkylphosphinate compounds of the present invention is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 5% to about 80%, and most preferably from about 10% to about 50%.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or lower animal in need of such treatment a safe and effective amount of a methylene phosphonoalkylphosphinate compound of the present invention.

The preferred mode of administration is oral, but other known methods of administration are contemplated as well, e.g., dermatomucosally (for example, dermally, sublingually, intranasally, rectally and the like), and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and subcutaneous administration, as well as topical application.

The term "abnormal calcium and phosphate metabolism", as used herein, means (1) conditions which are characterized by anomalous or age-related changes in bone metabolism and/or anomalous or age-related changes in calcium and phosphate metabolism leading to increased bone resorption, and/or general or specific loss of bone substance, and/or loss of bone structure, and/or loss of bone strength, or excessively high calcium and phosphate levels in the fluids of the body; and (2) conditions which cause or result from deposition of calcium and phosphate anomalously in the body. The first category includes, but is not limited to, osteopenia, osteoporosis, Paget's disease, hyperparathyroidism, hypercalcemia of malignancy, osteolytic bone metastases and the osteolytic lesions of arthritis such as rheumatoid arthritis and psoriatic arthritis. The second category includes, but is not limited to, myositis ossiticans progressiva, calcinosis universalis, and such afflictions as arthritis, osteoarthritis, neuritis, bursitis, tendonitis and other inflammatory conditions which predispose involved tissue to deposition of calcium phosphates.

The terms "person at risk" and "person in need of such treatment", as used herein, mean any human or lower animal which suffers a significant risk of abnormal calcium and phosphate metabolism if left untreated, and any human or lower animal diagnosed as being afflicted with abnormal calcium and phosphate metabolism. Examples of such persons include those having abnormal bone resorption: persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65. Other examples of such persons are those having abnormal tissue mineralization: persons being treated with drugs known to cause osteopetrosis as a side effect; persons diagnosed as suffering from myositis ossiticans progressiva or calcinosis universalis; and persons afflicted with arthritis, osteoarthritis, neuritis, bursitis, tendonitis and other inflammatory conditions which predispose involved tissue to deposition of calcium phosphate.

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of methylene phosphonoalkylphosphinate compounds of the present invention will vary with the particular condition being treated, the age and physical condition of the patient being treated, the severity of the condition, the duration of the treatment (including intermittent dosing regimens such as ADFR, pulsed dosing, etc.), the nature of concurrent therapy, the specific methylene phosphonoalkylphosphinate employed, the particular pharmaceutically-acceptable carrier utilized, and like factors within the knowledge and expertise of the attending physician. However, single dosages can range from about 0.01 mg P to about 3500 mg P, or from about 0.0002 to about 70 mg P/kg of body weight (based on a body weight of 50 kg). Preferred single dosages are from about 1 mg P to about 600 mg P, or from about 0.02 to about 12 mg P/kg of body weight (based on a body weight of 50 kg). Up to about four single dosages per day may be administered.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE 1

Thyroparathyroidectomized (TPTX) Rat Model

The compounds are evaluated for in vivo bone resorption inhibition potency by an animal model system known as the thyroparathyroidectomized (TPTX) rat model. The general principles of this model system are disclosed in Russell et al., *Calcif. Tissue Research*, 6, 183–196 (1970), and in Muhlbauer and Fleisch, *Mineral Electrolyte Metab.*, 5, 296–303 (1981), the disclosures of which are incorporated herein by reference in their entirety. The basic biochemical concept of the TPTX system is inhibition of the parathyroid hormone (PTH)-induced rise in serum total and ionized calcium levels by the respective bone active compounds.

(a) Materials

Low calcium and low phosphorous diets used are prepared by Teklad$^R$ Test Diets (Harlan Industries, Madison, Wis. 53711) in a pellet form of approximately 0.1 8% calcium and 0.22% phosphorous. The diets contain all the essential vitamins and minerals required for the rat, with the exception of calcium and phosphorous. The calcium and phosphorous levels of the pellets are verified analytically.

PTH is acquired as a powdered bovine extract (Sigma Chemical Co., P. O. Box 14508, St. Louis, Mo., order #P-4410). PTH is prepared in 0.9% saline such that the final concentration is 100 µg PTH/ml, or approximately 200 U.S.P. units/ml. All solutions are filtered through a #4 Whatman Filter Paper and refiltered through a 0.45 µm Metricel$^R$ filter.

(b) Dose Solutions and Dosing Procedure

All solutions of compounds to be tested for bone resorption inhibition potency are prepared for subcutaneous injection in 0.9% normal saline and adjusted to pH 7.4 using NaOH and/or HCl. Dose solution calculation is made by considering the mass of powder (based on molecular weight, hydration) of the active material in mg/kg (body weight) that corresponds to mg P/kg. Concentrations are based on dosing 0.2 ml/100 grams of body weight. Typically, all compounds are administered at 0.01, 0.1, and 1.0 mg P/kg/day for 4 days in order to determine the lowest effective dose ("LED"). Where necessary the test is repeated, whereby the animals are administered with 0.5 LED in order to refine the determination of LED. Adjustments in dosage based on changes in body weight are made on a daily basis.

(c) Animals

In this study 50 male Wistar rats weighing approximately 150–160 grams are thyroparathyroidectomized surgically by the breeder (Charles River Breeding Laboratories). All rats are double housed on arrival in suspended cages with Purina Laboratory Rodent Chow$^R$ and tap water ad libitum. After acclimation to the laboratory environment for 3–5 days, the rats are placed on a low calcium, low phosphorous (0.18%/

0.22%) diet (Teklad^R) and given 2% (W/V) calcium gluconate supplemented deionized water via water bottles.

(d) Method

On day three of low calcium diet, all rats are weighed. On day four, all rats are anesthetized with Ketaset^R (Ketamine Hydrochloride, 100 mg/ml, Bristol Myers), 0.10 ml/rat, and then bled from the retro-orbital venous plexus for serum total calcium analysis using Flame Atomic Absorption (FAA) or Nova 7+7 Automated Calcium Analyzer. All rats weighing less than 150 grams are eliminated from the study. Animals are then randomized statistically such that the mean total serum calcium for each group is the same. Only rats deemed hypocalcemic (total serum calcium <8.0 mg/dl) are placed in study groups comprising six to eight animals per group.

Treatments with the various experimental compounds commence on day 6 and last through day 9 of the study. Dose solutions are prepared to be given at a constant rate of 0.2 ml/100 grams of body weight subcutaneously in the vental skin flap where the hind leg meets the torso. All rats are weighed and dosed daily. A 25 gauge ⅝" needle is used to administer drug, alternating right and left dose sites daily. On day 8, animals are changed to deionized, distilled water via water bottles. On day 9 all rats are fasted in the afternoon at approximately 4:00 P.M. On day 10 of study no treatment is given. In the morning a 800 μl sample of whole blood is collected from each rat in Microtainer (B-D#5060) serum separator tubes for serum total and ionized calcium (FAA or Nova 7+7). Immediately following blood collection all rats are weighed and injected with bovin parathyroid hormone subcutaneously at a rate of 35 ug PTH per 100 grams of body weight. Blood sampling for total and ionized calcium is repeated three and one-half hours post-PTH injection.

All pre- and post-PTH total and ionized calciums from the treatment groups are statistically analyzed for significance compared to PTH alone (control) using Student's t-test, analysis of variance, and their non-parametric equivalents. This post minus pre-change is also determined on calcium levels and pre-drug vs post-drug body weights.

The physiological effect of the PTH challenge is a rise in serum calcium level, with peak activity observed at three to four hours. Since the hormonal and dietary controls of calcium metabolism are minimized in the TPTX model, an observed increase in serum calcium level is presumably the result of resorption of bone material. Since the compounds of the present invention tend to inhibit resorption of bone materials, the animals pretreated with these compounds show a rise in serum calcium level after PTH challenge which is less than that found in control animals which have been treated with saline vehicle instead. The lowest dose at which the experimental compound is capable of inhibiting bone resorption, as evidenced by a decreased rise in serum calcium upon PTH challenge, is a measure of the bone resorption inhibition potency of that compound. The LED values of the bone resorption inhibition potency of representative compounds as determined by the TPTX rat model are presented in Table 1. The data in Table 1 show that the compounds of the present invention are effective bone resorption inhibiting agents.

TABLE 1

Lowest Effective (Antiresorptive) Dose-TPTX Model

| Compound | TPTX LED (mg P/kg) |
| --- | --- |
| EHDP[1] | 1.0 |
| APD[2] | 0.1 |
| Cl₂MDP[3] | 1.0 |
| N-(2'-(3'-methyl)-pyridinyl)AMPMP[4]* | 1.0 |
| N-(2'-(5'-methyl)-pyridinyl)AMPMP[4]* | 0.1 |
| N-(2'-(3'-methyl)-piperidinylidene)AMPMP[4]* | 0.1 |
| N-(2'-(5'-methyl)-piperidinylidene)AMPMP[4]* | >0.1** |
| 2-(2'-pyridinyl)EPMP[5]* | 10 |
| 2-(2'-piperidinyl)EPMP[5]* | 1.0 |
| 2-(p-aminophenyl)EHPMP[6]* | >10** |
| 2-(m-aminophenyl)EHPMP[6]* | >1.0** |
| N-(1-(5-amino-2-methyl-1-oxo)-pentyl)-AMPMP[4]* | 10 |
| N-(2'-(3'-methyl)-piperidinylidene)AMPBP[7]* | 2.0 |
| S-(2'-pyridinyl)TMPMP[8]* | 10 |

*= Compound of the present invention.
**= Substantial activity not detected at the indicated dose, the highest dose tested
[1] ethane-1-hydroxy-1,1-diphosphonate
[2] 3-amino-propane-1-hydroxy-1,1-diphosphonate
[3] dichloromethane diphosphonate
[4] AMPMP = aminomethane phosphonomethylphosphinate
[5] EPMP = ethane-1-phosphono-1-methylphosphinate
[6] EHPMP = 1-hydroxy-ethane-1-phosphono-1-methylphosphinate
[7] AMPBP = aminomethane phosphonobutylphosphinate
[8] TMPMP = thiomethane phosphonomethylphosphinate

EXAMPLE 2

Schenk Model

The compounds are evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87–99 (1983); and in Schenk et al., *Calcif. Tissue Res.*, 11, 196–214 (1973), the disclosures of which are incorporated herein by reference in their entirety.

Materials and Methods

Animals

Preweaning 17-day-old (30 gms) male Sprague Dawley rats (Charles River Breeding Laboratories) are shipped with foster mothers and placed in plastic cages with their mothers upon arrival. At 19 days of age, pups receiving Rat Chow and water ad libitum are randomly allocated into treatment or control groups comprising seven animals per group. On day 1 and again on day 7 all animals are given an intraperitoneal ("IP") injection of Calcein (1% solution in 0.9% saline solution; dosed at 0.2 ml/100 g body weight). On day 4 all animals are given an IP injection of tetracycline hydrochloride (1% solution in 0.9% saline solution; dosed at 0.2 ml/100 g body weight). These compounds label actively mineralizing bone and cartilage.

Dose Solutions and Dosing Procedure

All solutions are prepared for subcutaneous injection in 0.9% normal saline and adjusted to pH 7.4 using NaOH and/or HCl. Dose solution calculation is made by considering the mass of powder (based on molecular weight, hydration) of the active material in mg/kg (body weight) that corresponds to mgP/kg. Concentrations are based on dosing 0.2 ml/100 g body weight. Typically, all compounds are administered at 0.01, 0.1, 1.0 and 10.0 mg P/kg/day over days 1 through 7. Compounds showing activity at 0.1 mg P/kg/day are then tested at logarithic decrements down to 0.001 mg/P/kg/day. Adjustments in dosage based on changes in body weight are made on a daily basis.

Necropsy, Tissue Processing, Absorptiometry and Histomorphometry

On day 8 after the start of dosing, all animals are sacrificed by IP overdose of pentabarbitol. Both tibias are dissected free and placed in 70% ethyl alcohol. The left tibias are analyzed for bone mineral content (BMC) by single beam photon absorptiometry (SPA) scanning, and the right tibias are dehydrated in graded ethanol solutions and embedded in methyl methacrylate as described in Schenk, *Methods of Calcified Tissue Preparation* (G. R. Dickson, Editor; Elsevier Science Publ., The Netherlands; 1984), the disclosures of which are incorporated herein by reference in their entirety. The left proximal tibias are evaluated by SPA to provide a measure of BMC. Since bone growth is accompanied by extensive bone resorption, an effective compound causes an increase in bone mass which is expressed as an increase in BMC. The right tibias are sectioned longitudinally through the metaphyseal area. Specimens are stained on one surface with silver nitrate and mounted on microscope slides for evaluation with a Quantimet Image Analyzer (Cambridge Instruments, Inc.) using both incandescent and ultraviolet illumination. Metaphyseal trabecular bone content is measured in the region between the fluorescent label and the growth plate: expressed as percent of total area (bone+marrow). An effective compound causes an increase in metaphyseal trabecular bone content. Epiphyseal growth plate width is obtained as the mean value of 10 equally-spaced measurements across the section.

Statistical evaluation of data is made using parametric and non-parametric analysis of variance and Wilcoxons rank sum test to determine a statistically significant effect compared to control animals.

The Schenk model provides data for in vivo bone resorption inhibition by the compounds. The lowest effective (antiresorptive) dose ("LED") for representative compounds tested, as determined by histology or SPA in the Schenk model, are provided in Table 2.

TABLE 2

Lowest Effective (Antiresorptive) Dose - Schenk Model

| Compound | Schenk LED (mg P/kg) |
|---|---|
| EHDP[1] | 1.0 |
| Cl$_2$MDP[2] | 1.0 |
| ADP[3] | 0.1 |
| N-(2'-(3'-methyl)-pyridinyl)AMPMP[4]* | 1.0 |
| N-(2'-(3'-methyl)-piperidinylidene)AMPMP[4]* | 0.1 |
| N-(2'-piperidinylidene)AMPMP[4]* | 10 |
| N-(2'-(5'-methyl)-piperidinylidene)AMPMP[5]* | >0.1** |
| 2-(2'-piperidinyl)EPMP[6]* | 1.0 |
| N-(2'-(5'-methyl)-pyridinyl)AMPMP[4]* | 1.0 |
| 2-(m-aminophenyl)EHPMP[5]* | >10** |

*= Compound of the present invention.
**= Substantial activity not detected at the indicated dose, the highest dose tested.
[1]ethane-1-hydroxy-1,1-diphosphonate
[2]dichloromethane diphosphonate
[3]3-amino-propane-1-hydroxy-1,1-diphosphonate
[4]AMPMP = aminomethane phosphonomethylphosphinate
[5]EHPMP = 1-hydroxy-ethane-1-1-phosphono-1-methylphosphinate
[6]EPMP = ethane-1-phosphono-1-methylphosphinate Compounds which have a bone mineralization inhibiting effect cause widening of the epiphyseal growth plate, since matrix production continues but mineralization is impeded. The widening of the epiphyseal growth plate as observed in the Schenk model is, therefore, a measure of the mineralization inhibiting effect of the compound tested.

EXAMPLE 3

Hydroxyapatite Crystal Growth Inhibition Test

The relative affinity of compounds for calcified tissues is demonstrated by the hydroxyapatite crystal growth inhibition test. This test was developed for polyphosphonates to establish their potential to reduce calcium phosphate deposition and has been shown to be predictive of the affinity of these compounds for calcified tissues like bone. The test is described in detail by Nancollas, et al., *Oral Biol.* 15, 731 (1970), the disclosures of which are incorporated herein by reference in their entirety.

In this test, hydroxyapatite seed crystals are added to a calcium/phosphate solution supersaturated with respect to induced precipitation of calcium phosphates but meta-stable toward spontaneous precipitation. The seed crystals induce precipitation and crystal growth. Test chemicals are added to the meta-stable Ca/P solution before seeding. The effect of these chemicals on formation of hydroxyapatite induced by seed crystals has been shown to correlate with in vivo effects of these chemicals on calcium metabolism.

Formation of calcium phosphate crystals results in the release of hydrogen ions (i.e., pH change). The rate of crystal growth is monitored by observing the addition of base required to maintain a constant pH. Low levels (about $10^{-5}$ to $10^{-6}$M) of phosphonoalkylphosphinates are capable of inhibiting the formation of calcium phosphate for 20 minutes or longer. Crystal growth inhibition depends on the propensity of the test compounds to adsorb on calcium phosphate crystal nuclei.

In the test, the time lapse $T_{lag}$ between addition of seed crystal and the start of crystal growth is measured. Often the $T_{lag}$ is measured at a constant concentration, such as $1'10^{-6}$M, in order to compare the relative activity of various compounds.

For the present purpose, the ability of the test compound to inhibit hydroxyapatite crystal growth is normalized relative to ethane-1-hydroxy-1,1-diphosphonic acid ("EHDP"). This normalization is achieved by dividing the concentration of the test compound necessary to exhibit a $T_{lag}$=50 minutes by the concentration of EHDP necessary to exhibit a $T_{lag}$=50 minutes. (The concentration of EHDP is determined along with the test compound and typically is approximately $1\times10^{-6}$M). Thus, the ability of the test compound to inhibit hydroxyapatite crystal growth relative to EHDP ("$I_R$") is calculated by:

$$I_R = \frac{[\text{concentration of test compound for } T_{lag} = 50 \text{ min.}]}{[\text{concentration of EHDP for } T_{lag} = 50 \text{ min.}]}$$

$I_R$ values for various compounds are provided in Table 3.

TABLE 3

Mineralization Inhibition (Crystal Growth Inhibition Test)

| Compound | $I_R$ |
|---|---|
| EHDP[1] | 1.0 |
| N-(2'-(3'-methyl)-pyridinyl)AMPMP[2]* | 27.5 |
| N-(2'-(3'-methyl)-pyridinyl)AMPBP[3]* | 26.9 |
| N-(2'-pyridinyl)AMPMP[2]* | 30.5 |
| N-(2'-(5'-methyl)-pyridinyl)AMPMP[2]* | 7.3 |
| N-(2'-(3'-methyl)-piperidinylidene)AMPMP[2]* | 46.4 |

TABLE 3-continued

Mineralization Inhibition (Crystal Growth Inhibition Test)

| Compound | $I_R$ |
|---|---|
| 2-(2'-pyridinyl)EPMP[4)]* | 63.6 |
| MPMP[5)]* | ~50 |
| 2-(phenyl)EHPMP[6)]* | 4.04 |
| 2-(p-aminophenyl)EHPMP[6)]* | 3.84 |
| EHPMP[6)]* | 5.93 |

*= Compounds of the present invention
[1)]ethane-1-hydroxy-1,1-diphosphonate
[2)]AMPMP = aminomethane phosphonomethylphosphinate
[3)]AMPBP = aminomethane phosphonobutylphosphinate
[4)]EPMP = ethane-1-phosphono-1-methylphosphinate
[5)]MPMP = methane phosphonomethylphosphinate
[6)]EHPMP = 1-hydroxy-ethane-1-phosphono-1-methylphosphinate

EXAMPLE 4

Synthesis of Methylene Phosphonomethylphosphinic Acid

A solution of methyl dichloro phosphine (50 gm; 0.43 moles) and ether (996 ml; dried over molecular sieves) is placed in a 2000 ml three neck round bottom flask, A solution of isopropanol (69.16 ml; 0.90 moles) and pyridine (72.47 ml; 0.90 moles) (both dried over molecular sieves) is then added dropwise under $N_2$ atmosphere via a dropping funnel to the reaction flask. (A mechanical stirrer is used throughout the reaction.) The temperature of the reaction is maintained at 20°–30° C. by cooling with an ice bath. After the addition is completed, the ice bath is removed and the reaction mixture is stirred at room temperature for 4 hours. The thick white precipitate which forms during the course of the reaction is then quickly filtered, washed with ether, and the filtrate is concentrated by rotary evaporation. This yields 55.35 gm of the clear oil diisopropylmethylphosphonite. $^{31}$P NMR ($CDCl_3$) 172 ppm.

A solution of diethyl iodomethyl phosphonate (54.85 gm; 0.20 moles; Lancaster Synthesis) and diisopropylmethylphosphonite (21.57 gm, 0.13 moles; which is prepared as described hereinbefore) is placed, under $N_2$ atmosphere, in a three neck flask equipped with a short path distillation head and dropping funnel. The solution temperature is then slowly increased via an oil bath. As soon as the isopropyl iodide starts to distill (124° C.), the remaining diisopropylmethylphosphonite (32.35 gm; 0.20 moles) is slowly added to the refluxing solution via the dropping funnel. The distillation is continued until the rate of reflux slows or until the distillate is no longer clear (about 150° C.). The remaining dark yellow solution is then transferred to a high vacuum distillation apparatus and distilled to remove the first cut of impurities. The undistilled oil is transferred to a Kugelrohr apparatus and the desired phosphonomethylphosphinate ester product is purified by Kugelrohr distillation (bp= 120°–150°, at 0.1 mm Hg). Several fractions are collected and the purity of each is determined by NMR. $^{31}$P NMR ($CDCl_3$): 18.50 (s); and 44.01 ppm (s) (some transesterification is noted). The yield of methylene phosphonomethylphosphinate ester is 15.05 gm.

This material is converted to methylene phosphonomethylphosphonic acid by refluxing the material overnight with 9N aqueous HCl followed by evaporation of the solvent.

EXAMPLE 5

Synthesis of 2-(2-Pyridyl)-Ethane-1-Phosphono-1-methylphosphinic Acid

Anhydrous DMSO (46 ml) is added to 1.45 gm sodium hydride in a 250 ml round bottom flask. The flask is placed in a cool water bath and methylene phosphonomethylphosphinate ester (8.45 gm; which is prepared as described hereinbefore in Example 4) dissolved in 29 ml of anhydrous DMSO, is added. The bath is removed after the addition and this solution is allowed to stir at room temperature for one hour.

In a second 250 ml round bottom flask, 17 ml of anhydrous DMSO and 1.45 gm of sodium hydride are combined. This flask is also cooled in a water bath and 2-picolyl chloride hydrochloride dissolved in 17.45 ml of anhydrous DMSO is added. The bath is removed after the addition, and the contents of the first flask is added to the second flask by syringe. The combined mixture is then heated at 85°–90° C. for about 1–1.5 hours, after which it is allowed to cool slowly to room temperature. The DMSO is evaporated off under high vacuum to yield the crude ester. This crude ester product is dissolved in $CH_2Cl_2$ (90 ml), washed with distilled water (3×30 ml) and then brine (1×30 ml). The methylene chloride layer is dried over $Na_2SO_4$ and filtered, and the filtrate is concentrated on the rotary evaporator to yield 8.68 gm of the desired ester.

4.08 gm of the 2-(2-pyridinyl)-ethane-1-phosphono-1-methylphosphinate ester is combined with 75 ml of 0.1N HCl and hydrolyzed overnight in an oil bath at approximately 110° C. under a nitrogen atmosphere. The acid solution is washed with methylene chloride (3×15 ml), and the aqueous layer is evaporated on a rotary evaporator. The resulting triacid is reevaporated with isopropanol several times to yield crude 2-(2-pyridinyl)-ethane-1-phosphono-1-methylphosphinic acid.

The crude product acid is dissolved in 25 ml of distilled water and titrated to the monosodium salt (pH=4.38). The aqueous solution is evaporated to yield 3.15 gm of the monosodium salt of 2-(2-pyridinyl)-ethane-1-phosphono-1-methylphosphinic acid. This salt is crystallized from 30 ml of ethanol to yield 1.46 gm of the desired product salt as a white powder after drying under vacuum. $^{31}$P NMR ($D_2O$): 40.01 ppm (s), 17.77 (s). $^1$H NMR ($D_2O$): 1.45 (d, J=17 Hz); 2.49 (m); 3.47 (m); 8.11 ppm (m). Anal. calc'd for $C_8H_{12}NNaO_5P_2 \cdot \frac{1}{2} H_2O \cdot NaCl$: C=27.10; H =3.70; N=3.95. Found: C=26.71; H=3.57; N=3.79.

EXAMPLE 6

Synthesis of 2-(2-Piperidinyl)-Ethane-1-Phosphono-1-methylphosphinic Acid

The monosodium salt of 2-(2-pyridinyl)-ethane-1-phosphono-1-methylphosphinic acid (1.27 gm; which is prepared as described hereinbefore in Example 5), Pt (IV) oxide (0.25 gm), and 63 ml of distilled water are placed in a 500 ml Parr hydrogenation bottle. This mixture is hydrogenated overnight at 40 psi. The mixture is filtered, washed with $H_2O$ and evaporated. After drying the collected solid under vacuum over night, 0.96 gm of the desired 2-(2-piperidinyl)-ethane-1-phosphono-1-methylphosphinic acid monosodium salt is isolated. $^{31}$P NMR ($D_2O$): 17.04 (d); 41.66 ppm (d). $^{13}$C NMR ($D_2O$): 18.60 (d, J=31 Hz; d, J=29

Hz); 24.53; 31.93; 32.25; 42.98; 46.83; 59.80 ppm. (mixture of diastereoisomers). Anal. calc'd for $C_8H_{18}NNaO_5P_2 \cdot \frac{1}{2}H_2O \cdot NaCl$: C=26.64; H=5.31; N=3.88. Cl=9.83; Found: C=26.06; H=5.02; N=3.78; Cl=9.0.

EXAMPLE 7

Synthesis of Methylene Phosphonobutylphosphinic Acid

Diethylchlorophosphite (18.8 gm, 0.12 moles) and 120 ml dry ether are combined in a round bottom flask equipped with a dropping funnel and under $N_2$ atmosphere. With a double tipped canula, butyl magnesium chloride (60 ml; 2.0M, 0.12 moles; Aldrich Chemical Co., Milwaukee, Wis.) is added to the dropping funnel. The round bottom flask is cooled in a salt water/ice bath and the contents of the dropping funnel are slowly added to the cooled flask. After the addition is complete, the bath is removed and the solution is allowed to stir at room temperature for three hours. The precipitate which forms during the course of the reaction is then quickly filtered and washed with ether. The filtrate is concentrated by rotary evaporator to yield 21.17 gm of diethylbutylphosphonite. $^{31}P$ NMR ($CDCl_3$): 182 ppm.

Diethylbutylphosphonite (11.30 gm, 0.064 moles; which is prepared as described hereinbefore) is used in the following Arbuzov reaction. One fifth of the diethylbutylphosphonite (2.26 gm, 0.013 moles) is added to a two neck round bottom flask equipped with a dropping funnel and a short path distillation head. Diethyl iodomethylphosphonate (12.01 gm, 0.042 moles; Lancaster Synthesis) is then added to this round bottom flask and this solution is heated with an oil bath. At 135° C., the distillate begins to come over. At this point, the remaining diethylbutylphosphonite (9.04 gm, 0.051 moles) is added to the reaction flask via the dropping funnel. The reaction temperature is steadily increased over the course of the reaction, and after the distillation ceases at 170° C., the external heat is removed and the round bottom flask is allowed to cool. The crude ester is then purified using Kugelrohr distillation apparatus. $^{31}P$ NMR ($CDCl_3$): 19.36 and 46.44 ppm.

The ester is converted to methylene phosphonobutylphosphinic acid by hydrolyzing under nitrogen for 4 hours at 110° C. with 9N HCl. (See Example 8.)

EXAMPLE 8

Synthesis of Methylene Phosphono(3'-butenyl)phosphinic acid ester

60% sodium hydride (0.49 gm, 12.13 mmoles) and 40 ml of dry ether are placed in a 100 ml round bottom flask under a nitrogen atmosphere. This solution is cooled to 0° C. in an ice bath, and then methylene phosphonomethylphosphinate ester (3.0 gm, 11.03 mmoles; which is prepared as described hereinbefore in Example 4) dissolved in 5 ml of ether is added via syringe. The resulting solution is allowed to slowly warm to room temperature over 45 minutes with stirring. After this time, the reaction is cooled to −78° C. in an acetone/dry ice bath, and 7.58 ml of 1.6M n-butyl lithium (12.13 moles) is added slowly via syringe. The reaction flask is transferred to an acetonitrile/dry ice bath and the cloudy solution is allowed to warm slowly to −40° C. over 45 minutes. 1,3-Dimethyl-2-imidazolidinone (2.17 ml, 19.85 mmoles) is added via syringe to the flask at −40° C. The solution is then allowed to warm to −30° C. while stirring over 20 minutes. Allyl bromide (0.95 ml, 11.03 mmoles) is added to the solution via syringe at −30° C. The reaction mixture is allowed to slowly come to room temperature over 1.75 hours, and then it is quenched with saturated ammonium chloride. This solution is washed with ether, and the ether layer is concentrated via rotary evaporator to yield 2.52 gm of crude methylene phosphono(3'-butenyl)phosphinic acid ester. This ester is chromatographed with 95/5 methylene chloride/ethanol. $^{31}P$ NMR ($CDCl_3$): 19.58 and 46.03 ppm.

This methylene phosphono(3'-butenyl)phosphinic acid ester may be converted to methylene phosphonobutylphosphinic acid ester by hydrogenation. Thus, 56 mg of the ester, 10 ml of ethanol, and 89 mg Pd/C are placed in a 200 ml Parr hydrogenation bottle and this mixture is hydrogenated overnight at 40 psi. The solution is filtered and the filter is washed with hot ethanol. The filtrate is evaporated to yield 50 mg of methylene phosphonobutylphosphinic acid ester. This material is hydrolyzed under nitrogen for 4 hours at 110° C. with 5 ml of 9N HCl to yield the methylene phosphonobutylphosphinic acid as in Example 7. $^{31}P$ NMR ($D_2O$; pH=12): 12.26; 41.82 ppm.

EXAMPLE 9

Synthesis of Methylene Phosphono(trifluoromethyl)phosphinic Acid

To a mixture of diethyl chloro phosphite (1 mmole) and bromo trifluoromethane (1 mmole) is added tris(diethylamino) phosphine (1 mmole) dropwise. After the reaction is complete, the desired diethyl trifluoromethyl phosphonite is distilled to purity. (See Maslennikov, I. G., A. N. Lavrent'ev, N. V. Khovanskaya, V. B. Lebedev & E. G. Sochilin, "Perfluoroalkyl phosphonous acid esters", *Zh. Obshch. Khim*, Vol. 49, No. 7 (1979), pp. 1498–1501, which is hereby incorporated by reference.) This material is then used in place of diethyl methyl phosphonite to prepare methylene phosphono(trifluoromethyl) phosphinic acid by the reaction sequence as described in Example 4 for the synthesis of methylene phosphonomethylphosphinic acid.

EXAMPLE 10

Synthesis of 2-(Phenyl)-Ethane-1-Hydroxy-1-Phosphono-1-methylphosphinic Acid

Phenylacetyl chloride (15.46 gm, 0.10 moles) is placed in a round bottom flask with a stir bar under a nitrogen atmosphere and cooled to 0° C. Trimethylphosphite (12.42 gm; 0.01 moles) is added dropwise to the reaction flask. The reaction mixture is then warmed to room temperature and stirring is continued for 2 hours. The white precipitate which forms is filtered, washed with ether, and recrystallized from hot ethyl acetate to yield 9 gm of dimethyl phenylacylphosphonate (Nicholson, D. A., & H. Vaughn, *J. Org. Chem.*, 36(24) 3843 (1971), incorporated by reference herein in its entirety). $^{31}P$ NMR ($CDCl_3$): 16.513 ppm (s).

Dimethyl phenylacylphosphonate (4.4 gm; 0.019 moles) is added slowly to ethyl hydrogen methylphosphinate (2.09 gm, 0.019 moles) (see Daugherty, K. E., A. Eychaner, J. I. Stevens, *Applied Spectroscopy*, 22 (2), 96 (1968), which is incorporated herein by reference in its entirety) at room temperature in a round bottom flask under nitrogen atmosphere. This mixture is then heated to about 55°–60° C. and allowed to stir for 11 hours to yield trimethyl 2-(phenyl)- ethane-1-hydroxy-1-phosphono-1-methylphosphinate, which is immediately hydrolyzed in 6N HCl to the free acid. The pH is then brought to pH=4.5 with 1N NaOH to yield the disodium salt of 2-(phenyl)-ethane-1-hydroxy-1-phosphono-1-methylphosphinic acid after recrystallizing from ethanol and water. $^{31}$P NMR (D$_2$O): 42.16 (d, J=22 Hz); 17.79 ppm (d, J=22 Hz);$^1$H NMR (D$_2$O): 7.39–7.30(m, 5H); 3.23(t, 2H, J=12 Hz); 1.10 ppm (d, J=14 Hz). Anal. calc'd. for Na$_2$C$_9$H$_{12}$O$_6$P$_2$.½H$_2$O: C=32.45; H=3.93. Found: C=32.63; H=3.71.

EXAMPLE 11

Synthesis of Methylene Phosphono(1'-(2'-phenyl)ethyl)phosphinic Acid

Triethyl methylene phosphonomethylphosphinate (0.28 gm; 1.10 mmoles) dissolved in 0.5 ml THF is added to a solution of NaH (60%; 0.048 gm; 1.21 mmoles) and ether (4 ml) cooled to 0° C. The solution is then allowed to slowly come to room temperature over 45 minutes with stirring. The reaction is then cooled to –78° C. with an acetone/dry ice bath and n-butyl lithium (0.76 ml, 1.21 mmoles) is added slowly via syringe. This mixture is allowed to warm to –40° C. with an acetonitrile/dry ice bath and then 1,3-dimethyl-2-imidazolidinone (0.22 ml; 1.98 moles) is added via syringe. Next, the reaction is allowed to warm to –30° C. and benzyl bromide (0.13 ml; 1.10 moles) is added by a syringe. The reaction mixture is allowed to stir at this temperature for two hours, after which time it is quenched with 4 ml ammonium chloride and extracted with ether. The ether layer is concentrated on a rotary evaporator to yield 0.44 gm crude ester product. This ester is separated by silica gel chromatography. $^{31}$P NMR (CDCl$_3$): 20.60; 46.44 ppm.

The ester is hydrolyzed with 6N HCl at 110° C. overnight to yield the methylene phosphono((2'-phenyl)ethyl)phosphinic acid. $^{31}$P NMR (D$_2$O): 15.63; 47.41 ppm.

EXAMPLE 12

Synthesis of S-(2'-Pyridyl)-Thiomethyl-Phosphonomethylphosphinic Acid

Potassium hydride (35%; 1.36 gm; 0.01 moles) is placed in a two neck round bottom flask with 50 ml of distilled toluene. The flask is then cooled in an ice bath, and methylene phosphonomethylphosphinate ester (2.27 gm; 0.01 moles; which is prepared as described in Example 4 hereinbefore) is added dropwise over a 15 minute period. The ice bath is removed after the addition, and the solution is then stirred at room temperature for 1 hour. After this hour, the round bottom flask is again cooled to 0° C. in an ice bath and 2,2'-dipyridinyldisulfide (2.20 gm; 0.01 mole; Aldrich Chemical Co.) dissolved in 30 ml dry toluene is quickly added to the reaction flask. This solution is stirred at 0° C. for 1 hour and then a second equivalent of potassium hydride (1.36 gm; 0.01 moles) is added to the reaction flask. The solution is allowed to gradually come to room temperature, and is stirred overnight under ambient conditions. The solution is then filtered through celite and the filtrate is evaporated via rotary evaporator to yield a yellow oil as the crude ester product. This crude product is purified by chromatography in a 75:25 mixture of acetone:hexanes. The purity of the ester is determined by NMR. Yield of pure product is 1.91 gm. $^{31}$P NMR (CDCl$_3$): 19.16; 44.91 ppm.

1.49 gm of the pure ester is hydrolyzed overnight in 3N HCl (50 ml). The solution is concentrated by rotary evaporator, and the product is re-evaporated with isopropanol several times. The resulting solid is recrystallized with acetone to yield 0.80 gm of S-(2'-pyridinyl)-thiomethyl-phosphonomethylphosphinic acid. $^{31}$P NMR (D$_2$O):10.67; 40.57 ppm. $^1$H NMR (D$_2$O; pD=11): 1.51 (3H, d, J=14 Hz); 3.75 (1H, dd, J=19 Hz; J=20 Hz); 7.13–7.80 (3H, m); 8.39 ppm (1H, d). Anal. calc'd. for C$_7$H$_{11}$NO$_5$P$_2$S.H$_2$O: C=27.91; H=4.35; N=4.65. Found: C=28.27; H=4.08; N=4.65.

EXAMPLE 13

Synthesis of N-(2'-(3'-methyl)-pyridinyl)-Aminomethane Phosphonomethylphosphinic Acid (a) Procedure A:

Ethyl hydrogen methylphosphinate (49 mmole; see Example 10) is combined with diisopropyl phosphite (8.1 ml; 49 mmole), 2-amino-3-methylpyridine (5.3 gm; 49 mmole), and triethyl orthoformate (10 ml; 49 mmole) in a flask equipped with a magnetic stirring bar, a distillation head, and under argon atmosphere. The reaction mixture is then brought slowly to 150°–160° C. and maintained at this temperature for one hour while ethanol distills from the reaction flask. The reaction mixture is then cooled and chromatographed on medium pressure chromatography apparatus with a gradiant of 5–15% ethanol/methylene chloride to yield 3.0 gm of the desired N-(2'-(3'-methyl)-pyridinyl)-aminoethane phosphonomethylphosphinate triester. (A mixture of isopropyl and ethyl esters are isolated due to transesterification.) $^{31}$P NMR (CDCl$_3$): 45.4 (m); 17.5 (m).

The ester mixture (0.9 gm) is refluxed in 4 ml of water for one hour, and the resulting white precipitate is filtered and dried to yield 0.5 gm of desired N-(2'-(3'-methyl)-pyridinyl)-aminomethane phosphonomethylphosphinic acid.

(b) Procedure B:

To a flask containing triethyl orthoformate (23.6 gm; 0.16 mole) equipped with a magnetic stirrer, condensor, and nitrogen atmosphere, is added diethyl chloro phosphite (25 gm; 0.16 mole) over 15–30 minutes and an extremely exothermic reaction occurs. The reaction solution is then heated at 135° C. for 3 hours. The resulting solution is distilled using a Kugelrohr distillation apparatus at 80° C. (0.01 mm Hg) to yield 32 gm of diethoxymethylphosphonic acid diethyl ester ($^{31}$P NMR 13.2 ppm).

This ester (15 gm, 62.5 mmole) is combined with ethyl hydrogen methylphosphinate (9.6 gm; 62.5 mmole; see Example 10) and 2-amino-3-methylpyridine (6.75 gm; 62.5 mmole) in a flask equipped with a short path distillation head, magnetic stirrer, and a nitrogen atmosphere. The flask is placed in an oil bath and the temperature is slowly brought to 150° C. The reaction mixture is kept at this temperature until no further ethanol is distilled off (approximately 30 minutes), and then the mixture is heated at 170°–175° C. for 4 to 5 hours. After this time, the bath temperature is cooled to 110° C., 75 ml of water is added, and this reaction mixture is allowed to reflux for one hour. The resulting white precipitate is collected, rinsed with hot water (2×10 ml), and dried to yield 5.7 gm of N-(2'-(3'-methyl)-pyridinyl)-aminoethane phosphonomethylphosphinic acid.

The monosodium salt is prepared by the addition of one equivalent of 6N NaOH to bring a 10% aqueous solution to a pH of 4.0. $^1$H NMR (D$_2$O; 1 equivalent NaOH ): 7.69 (1H, d, J=7.2 Hz ); 7.65 (1H, d, J=6.3 Hz); 6.8 (1H, dd); 4.0 (1H, dd, J=20.1 Hz, J=15.6 Hz); 2.23(3H, s); 1.42 ppm (3H, d, J=14.4 Hz). $^{31}$P NMR: 35.11 (d, J=15 Hz); 11.54 ppm (d, J=15 Hz). Anal. calc'd. for $C_8H_{14}N_2O_5P_2$: C=34.30; H=5.04; N=10.00. Found: C=34.54; H=5.30; N=9.79.

EXAMPLE 14

Synthesis of N-(2'-(3'-methyl)-piperidinylidene)-Aminomethane Phosphonomethylphosphinic Acid, Monosodium Salt To a 10% aqueous solution of N-(2'-(3'-methyl)-pyridinyl)-aminomethane phosphonomethylphosphinic acid (41g) is added 6N NaOH until the pH is adjusted to 4.0. The resulting solution is diluted to 820 ml water and hydrogenated for 48 hours at 50 psi at room temperature with 12 gm of 10% Pd/C in a Parr hydrogenation apparatus. The solution is then filtered and evaporated to dryness to yield 43 gm of N-(2'-(3'-methyl)-piperidinylidene)-aminomethane phosphonomethylphosphinic acid, monosodium salt. The following spectral data are reported on the 1:1 mixture of diastereoisomers. $^{31}$P NMR (2.5% in $D_2O$): 33.37 (d, J=13Hz) 32.93 (d, J=13Hz), 9.99 (d, J=13Hz), 9.66 (d, J=13Hz). $^1$H NMR (1% in $D_2O$): 3.88 (1H, dd, J=15.6, 19.9); 3.45 (2H, m); 2.92 (1H, m); 1.96 (2H, m); 1.82 (1H, m); 1.66 (1H, m); 1.46 (1.5H, d, J=14.5); 1.44 (1.5H, d, J=13.9); 1.40 (1.5H, d, J=6.9); 1.39 ppm (1.5H, d, J=6.8). $^{13}$C NMR (10% in $D_2O$): 169.6, 55.7 (2 overlapping dd's), 44.0, 33.3, 27.7, 20.6, 19.5, 17.7 (d, J=98). Anal. calc'd. for $C_8H_{17}N_2O_5P_2Na\ H_2O$: C=29.63; H=5.91; N=8.64. Found: C=30.06; H=6.31; N=8.77.

EXAMPLE 15

Synthesis of N-(1-(5-amino-2-methyl-1-oxo)-pentyl)-Aminomethane Phosphonomethylphosphinic Acid A 10% aqueous solution of sodium N-(2'-(3'-methyl)-piperidinylidene)-amino methane-1-phosphono-1-methylphosphinate (10 g) is refluxed for 72 hours under a nitrogen atmosphere. After noting approximately a 75% conversion to new material, pure N-(1-(5-amino-2-methyl-1-oxo)-pentyl)-aminomethane-1-phosphono-1-methylphosphinic acid is isolated on a preparative HPLC silica gel column on elution with approximately 91:9 $MeOH/H_2O$. The product isolated is reported as a 1:1 mixture of diastereoisomers. $^{31}$P NMR ($D_2O$, pD=12): 35, 12 ppm. $^{13}$C NMR (10% in $D_2O$): 180.4, 52.2 (2 overlapping dd's), 42.5, 41.4, 32.4, 26.9, 19.2, 17.6 (d, J=96). $^1$H NMR (1% in $D_2O$): 4.35 (1H, m), 3.00 (2H, m), 2.55 (1H, m), 1.58 (2H, m), 1.53 (1H, m), 1.39 (1.5H, d, J=14.0), 1.36 (1.5H, d, J=14.0), 1.17 (1.5H, d, J=6.8), 1.16 (1.5H, d, J=6.8).

EXAMPLE 16

Synthesis of 1-Dihydropyrindine-6,6-phosphonomethyl-phosphinic Acid

To an ice bath chilled solution of potassium hydride (35% in mineral oil; 5.2 grams; 0.045 moles) in 70 ml of anhydrous DMSO stirring under argon atmosphere is added dropwise a solution of triethyl methylene phosphonomethylphosphinate (5.9 grams; 0.023 moles; which is prepared as described hereinbefore in Example 4) in 30 ml of anhydrous DMSO. After completion of the addition, the resulting solution is stirred at room temperature for one hour. A solution of 2,3-bis(chloromethyl)pyridine (4.0 grams; 0.023 moles; a crude product as isolated by Tsuda et al., *Chem. Pharm. Bull.*, 1, page 142 (1953)) in 15 ml of anhydrous DMSO is then added slowly, and the reaction mixture is heated at 90° C. for 1 hour. The reaction mixture is allowed to cool, the solvent is evaporated under high vacuum, and the resulting crude product is chromatographed (5%–10% ethanol/methylenechloride). $^{31}$P NMR ($CDCl_3$): 27.25, 52.79 ppm.

The product ester is refluxed with 6N HCl while stirring under an argon atmosphere for 18 hours. The solvent is then removed to yield the desired acid product.

EXAMPLE 17

Synthesis of 1-Octahydropyrindine-6,6-phosphonomethyl-phosphinic Acid

1-Dihydropyrindine-6,6-phosphonomethylphosphinic acid (which is prepared as in Example 16) is combined with distilled water and $PtO_2$ in a 500 ml Parr hydrogenation bottle. This mixture is hydrogenated at room temperature (40 psi) for 2 days. The solution is then filtered and washed with hot distilled water. The filtrate is concentrated on a rotary evaporator, and the resulting product 1-octahydropyrindine-6,6-phosphonomethylphosphinic acid is dried under vacuum overnight.

EXAMPLE 18

5-(N-glycyl)aminopentane-1-hydroxy-1-phosphono-1-methylphosphinic acid

Chlorovaleric acid (5.0 g, 0.037 moles) is dissolved in 40ml of dry methylene chloride in a round bottom flask under a nitrogen atmosphere. Freshly distilled oxalyl chloride (9.58 ml, 0.110 moles) is added and the mixture is stirred overnight. The solution is concentrated under vacuum to dryness to yield 5.15 g of chlorovaleryl chloride. Trimethylphosphite (3.9 ml, 0.033 mole) is slowly added to chlorovaleryl chloride (5.15 g, 0.033 mole) under a continuous flow of nitrogen. The mixture is allowed to stir overnight to yield 7.15 g of dimethyl chlorovalerylphosphonate.

Ethyl hydrogen methylphosphonate (3.10 g, 0. 029 mole) is added slowly to dimethyl chlorovalerylphosphonate (6.51 g, 0.029 mole) at room temperature in a round bottom flask under a nitrogen atmosphere. This mixture is then heated to 55°–60° C. and allowed to stir overnight to yield ethyldimethyl 5-chloropentane-1-hydroxy-1-phosphono-1-methylphosphinic acid.

Ethyldimethyl 5-chloropentane-1-hydroxy-1-phosphono-1-methylphosphinic acid (9.86 g, 0.029 mole) is dissolved in 30 ml of dry chloroform in a round bottom flask under a nitrogen atmosphere. Freshly distilled trimethylsilyl bromide (22.8 ml, 0.17 mole) is slowly added and the solution stirred overnight. This solution is concentrated under vacuum and after excess methanol is added the mixture is allowed to stir for 1 hour. The precipitate that forms is filtered and washed with ether to yield 5-chloropentane-1-hydroxy-1-phosphono-1-methylphosphinic acid.

5-Chloropentane-1-hydroxy-1-phosphono-1-methylphosphinic acid is added to excess ammonium hydroxide and allowed to stir overnight at 50° C. Ethanol is then added to the warm solution to allow 5-aminopentane-1-hydroxy-1- phosphono-1-methylphosphinic acid to precipitate. The desired product is then separated and dried.

Na₃ 5-aminopentane-1-hydroxy-1-phosphono-1-methylphosphinic acid (4 g, 0.015 mole) in 40 ml of water is treated with phthaloyl-glycyl chloride (4 g, 0.018 Mole), simultaneously adding 1N NaOH to maintain pH 11–12. After stirring 1 hours, the mixture is treated with Dowex-50W resin (acid form) to pH 1.4, the ion-exchange resin filtered off and acetone added to precipitate 5-(N-phthaloylglycyl)aminopentane-1-hydroxy-1-phosphono-1-methylphosphinic acid. 2 g of this is dissolved in 20 ml of water, treated with 0.5 ml of acetic acid and 0.9 ml of phenylhydrazine, stirred for 5 hr at 50° C., and then cooled and filtered. The filtrate is stirred into methanol to give 5-(N-glycyl)aminopentane-1-hydroxy-1-phosphono-1-methylphosphinic acid.

EXAMPLE 19

N-(3-Methylphosphinyl-1-oxo-3-phosphonopropyl)glycine

To a suspension of potassium hydride (15 mmol; 1.72 g) in anhydrous toluene (15 ml) under an $N_2$ atmosphere is added phosphonomethylphosphinate ester (10 mmol; 2.72 g), which is prepared as described hereinbefore in Example 4, in dry toluene (10 ml) dropwise. After stirring for 45 minutes at 22° C., the excess potassium hydride is allowed to settle and the solution of the anion is added dropwise via cannulla to a solution of ethyl bromoacetate (10 mmol; 1.67 g) in dry toluene (10 ml). After stirring overnight at 22° C., the reaction is quenched with saturated aqueous ammonium chloride (30 ml) and extracted with ether (3×40 ml). The combined organic extracts are washed with brine and dried ($Na_2SO_4$). Filtration and concentration in vacuo gives the desired compound.

A suspension of the above ester (10 mmol) in 1N NaOH (10mmol) is heated to 80° C. for 1.5 hr. The homogeneous mixture is then cooled to room temperature and 1NHCl (10 ml) is added. The reaction is concentrated in vacuo to give a solid which is slurried with methylene chloride (75 ml). The methylene chloride is decanted and concentrated in vacuo to give the carboxylic acid.

The above carboxylic acid (5 mmol) is dissolved in dry methylene chloride (10 ml) and freshly distilled oxalyl chloride (7.5 mmol) is added dropwise under an $N_2$ atmosphere. After stirring overnight, the reaction is concentrated in vacuo to yield the acid chloride.

The above acid chloride (2 mmol) is dissolved in dry ether (5 ml) and added portionwise to a suspension of glycine ethyl ester hydrochloride (3 mmol) in dry ether (10 ml) containing triethyl amine (6 mmol) and stirred overnight. The precipitate is collected on a filter, washed with ether, and triturated and washed with water to extract the triethylammonium chloride. The desired product is obtained after drying overnight.

To a solution of the above compound (2 mmol) in dry chloroform (5 ml) is added freshly distilled iodotrimethyl silane (10 mmol) at 0° C. under an $N_2$ atmosphere. The reaction is slowly warmed to room temperature and stirred overnight. It is then concentrated in vacuo. Methanol (10 ml) is added and the reaction stirred for 1 hr. The precipitate which forms is collected, washed with cold methanol and dried to yield the title compound.

EXAMPLE 20

Ethenylidene-1-phosphono-1-methylphosphinate

Paraformaldehyde (10.4 g) and diethylamine (5.0 g, 0.07 mol) are combined in 240 ml of methanol and the mixture is warmed until clear. The heat is removed and phosphonomethylphosphonate ester (Example 4) is added. The mixture is refluxed for 24 hr, then an additional 200 ml of methanol is added and the solution is concentrated under vacuum. Toluene (100 ml) is added and the solution again concentrated. This last step is repeated to ensure complete removal of methanol from the product, the 2-methoxyethane-1-phosphono-1-methylphosphinate triester, which is obtained as a clear liquid.

This triester is then dissolved in 100 ml of dry toluene. p-Toluenesulfonic acid monohydrate (0.05 g) is added and the mixture is refluxed. Methanol is removed from the reaction mixture by collection in a Dean-Stark trap. After refluxing for 48 hr, the solution is concentrated. The crude product is diluted with 150 ml of chloroform and washed with water (2×35 ml). The chloroform solution is dried over $MgSO_4$ and concentrated. Distillation affords pure ethylenylidene-1-phosphono-1-methylphosphinate triester.

Bromotrimethylsilane is added via syringe to a solution of the above triester in dry $CCl_4$. The mixture is stirred for ca. 72 hr, then concentrated. The crude product is dissolved in methanol and precipitated by the addition of methanolic KOH solution. The mixture is filtered. The precipitate is washed with methanol and then dried under vacuum. The white solid product is dissolved in water and stirred overnight with excess Rexyn 101 (H) resin (Fisher). The solution is freeze-dried to afford the desired ethenylidene-1-phosphono-1-methylphosphinate.

EXAMPLE 21

Capsules are prepared by conventional methods, comprised as follows:

| Ingredient | Mg per Capsule |
| --- | --- |
| N-(2'-(3'-methyl)-piperidinylidene)aminomethane phosphonomethylphosphinic acid | 25 (as mgP) |
| Starch | 55.60 |
| Sodium lauryl sulfate | 2.90 |

The above capsules administered orally twice daily for 6 months substantially reduce bone resorption in a patient weighing approximately 70 kilograms afflicted with osteoporosis. Similar results are obtained when N-(2'-(3'-methyl)-piperidinylidene)aminoethane-phosphonomethylphosphinic acid in the above described capsules is replaced with N-(2'-(3'-methyl)-pyridinyl)aminoethane-phosphonomethylphosphinic acid; 2-(2'-pyridinyl)ethane-1-phosphono-1-methylphosphinic acid; 2-(2'-piperidinyl)ethane-1-phosphono-1-methylphosphinic acid; N-(1-(5-amino-2-methyl- 1-oxo)-pentyl)-aminomethane-phosphonomethylphosphinic acid; N-(2'-(3'-methyl)-piperidinylidene)-aminomethane-phosphonobutylphosphinic acid; S-(2'-pyridinyl)-thiomethane-phosphonomethylphosphinic acid; or a pharmaceutically-acceptable salt or ester of these compounds.

EXAMPLE 22

Tablets are prepared by conventional methods, formulated as follows:

| Ingredient | Mg per tablet |
| --- | --- |
| N-(2'-(3'-methyl)-piperidinylidene)amino-methane phosphonomethylphosphinic acid | 25 (as mgP) |
| Lactose | 40 |
| Starch | 2.5 |
| Magnesium stearate | 1 |

The above tablets administered orally twice daily for 6 months substantially reduce bone resorption in a patient weighing approximately 70 kilograms afflicted with Paget's disease. Similar results are obtained when N-(2'-(3'-methyl)-piperidinylidene)- aminomethane-phosphonomethylphosphinic acid in the above described tablets is replaced with N-(2'-(3'-methyl)-pyridinyl)-aminomethane-phosphonomethylphosphinic acid; 2-(2'-pyridinyl)-ethane-1-phosphono-1-methylphosphinic acid; 2-(2'-piperidinyl)-ethane-1-phosphono-1-methylphosphinic acid; N-(1-(5-amino-2-methyl-1-oxo)-pentyl)-aminomethane-phosphonomethylphosphinic acid; N-(2'-(3'-methyl)-piperidinylidene)-aminomethane-phosphonobutylphosphinic acid; S-(2'-pyridinyl)-thiomethane-phosphonomethylphosphinic acid; or a pharmaceutically-acceptable salt or ester of these compounds.

EXAMPLE 23

Patients weighing approximately 70 kilograms who are clinically diagnosed as suffering from hypercalcemia of malignancy are administered 15 mg P of 2-(2'-piperidinyl)-ethane-1-phosphono-1-methylphosphinic acid, or its pharmaceutically-acceptable salt or ester, by a 2½ hour intravenous infusion one time daily for 4 days. This treatment results in an appreciable alleviation of the hypercalcemia of malignancy.

EXAMPLE 24

Tablets are prepared by conventional methods, formulated to contain N-(2'-(3'-methyl)-piperidinylidene aminomethane phosphonomethylphosphinic acid as described in Example 21, and administered orally in an intermittent cyclic regimen such as two tablets daily for 14 days, followed by a 3-month drug-free interval in which a patient may also receive a daily calcium supplement in the range of approximately 500 mg to 1000 mg per day. Such an intermittent cyclic dosing regimen of 14 days of drug administration followed by 3 months of daily calcium supplementation is repeated for 3 years, resulting in an overall reduction in bone resorption and a stabilization or a substantial increase in bone density and or bone strength in a patient weighing approximately 70 kilograms afflicted with osteoporosis. Similar results are obtained when N-(2'-(3'-methyl)-piperidinylidene)aminoethane-phosphonomethylphosphinic acid in the above described tablets is replaced with N-(2'-(3'-methyl)-pyridinyl)aminoethane-phosphonomethylphosphinic acid; 2-(2'-pyridinyl)ethane-1-phosphono-1-methylphosphinic acid; 2-(2'-piperidinyl)ethane-1-phosphono-1-methylphosphinic acid; N-(1-(5-amino-2-methyl-1-oxo)-pentyl)-aminomethane-phosphonomethylphosphinic acid; N-(2'-(3'-methyl)-piperidinylidene)-aminomethane-phosphonobutylphosphinic acid; S-(2'-pyridinyl)-thiomethane-phosphonomethylphosphinic acid; or a pharmaceutically-acceptable salt or ester of these compounds.

EXAMPLE 25

Tablets are prepared by conventional methods, formulated to contain N-(2'-(3'-methyl)-piperidinylidene aminomethane phosphonomethylphosphinic acid as described in Example 21, and administered orally twice daily for 6 months substantially reducing pathologic bone resorption and reducing pathologic deposition of calcium phosphates in inflamed tissues in a patient weighing approximately 70 kilograms afflicted with rheumatoid arthritis. Similar results are obtained when N-(2'-(3'-methyl)-piperidinylidene)-aminoethane-phosphonomethylphosphinic acid in the above described tablets is replaced with N-(2'-(3'-methyl)-pyridinyl)aminoethane-phosphonomethylphosphinic acid; 2-(2'-pyridinyl)-ethane-1-phosphono-1-methylphosphinic acid; 2-(2'-piperidinyl)-ethane-1-phosphono-1-methylphosphonic acid; N-(1-(5-amino-2-methyl-1-oxo)-pentyl)-aminomethane-phosphonomethylphosphinic acid; N-(2'-(3'-methyl)-piperidinylidene)-aminomethane-phosphonobutylphosphinic acid; S-(2'-pyridinyl)-thiomethane-phosphonomethylphosphinic acid; or a pharmaceutically-acceptable salt or ester of these compounds.

EXAMPLE 26

Tablets are prepared by conventional methods, formulated to contain N-(2'-(3'-methyl)-piperidinylidene aminomethane phosphonomethylphosphinic acid as described in Example 21, and administered orally twice daily for 12 months substantially reducing bone resorption, reducing the development of new metastatic lesions to bone, and or reducing the progression of existing metastatic bone lesions in a patient weighting approximately 70 kilograms afflicted with a malignant tumor originating in, but not limited to the breasts, lungs, kidneys, prostate or colon, or afflicted with a hemotologic malignancy including, but not limited to myeloma or lymphoma. This treatment also results in a substantial reduction in the various sequella associated with metastatic bone involvement such as hypercalcemia of malignancy, bone fractures, and bone pain. Similar results are obtained when N-(2'-(3'-methyl)-piperidinylidene-aminomethane-phosphonomethylphosphinic acid in the above described tablets is replaced with N-(2'-(3'-methyl-pyridinyl)-aminomethane-phosphonomethylphosphinic acid; 2-(2'-pyridinyl)-ethane-1-phosphono-1-methylphosphinic acid; N-(1-(5-amino-2-methyl-1-oxo)-pentyl)-aminomethane-phosphonomethylphosphinic acid; N-(2'-(3'-methyl)-piperidinylidene)-aminoethane-phosphonobutyl-phosphinic acid; S-(2'-pyridinyl)thiomethane-phosphonomethylphosphinic acid; or a pharmaceutically-acceptable salt or ester of these compounds.

What is claimed is:

1. A methylene phosphonoalkylphosphinic acid compound having the following structure:

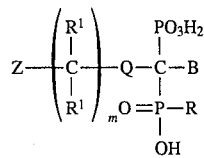

wherein (a) m is an integer from 0 to 10;

(b) Q is NR²; where R² is selected from the group consisting of hydrogen, lower alkyl, and lower alkyl acyl, or is replaced by a second bond between the nitrogen which it is on and an adjacent atom capable of accepting a second bond;

(c) is a moiety selected from the group consisting of hydrogen and unsubstituted and substituted alkyl; wherein said substituents in the substituted alkyl include halogen, unsubstituted and substituted phenyl, unsubstituted and substituted pyridinyl, unsubstituted amino, amino substituted with one or two lower alkyl groups, hydroxy, carboxy, and chemically-stable combinations thereof;

(d) B is a moiety selected from the group consisting of hydrogen; unsubstituted and substituted lower alkyl; unsubstituted and substituted cycloalkyl having from 3 to 7 atoms in the ring; unsubstituted and substituted heterocycles having 5 or 6 atoms in the ring and 1—3 heteroatoms selected from O, S, P, or N; unsubstituted and substituted phenyl; —CO₂H, the pharmaceutically-acceptable salts thereof, the pharmaceutically-acceptable lower alkyl esters thereof, the unsubstituted amide thereof, and the amide thereof substituted with one or two lower alkyl groups;

wherein said substituted alkyls and substituted $C_1$–$C_6$ cycloalkyls are substituted with with a member selected from the group consisting of alkyl; halogen; nitro; cyano; heterocycle; aryl; heteroaryl; unsubstituted amino, the alkyl amides thereof, the heterocycle amides thereof, the aryl amides thereof, or the heteroaryl amides thereof; amino substituted with one alkyl, heterocycle, aryl or heteroaryl group and the alkyl amides thereof; amino substituted independently with one alkyl group and one alkyl, heterocycle, aryl or heteroaryl group; hydroxy, the alkyl esters thereof, the heterocycle esters thereof, the aryl esters thereof, or the heteroaryl esters thereof; ether having an alkyl, heterocycle, aryl or heteroaryl group; thiol, alkyl thiol esters, heterocycle thiol esters, aryl thiol esters, and heteroaryl thiol esters; thioether having an alkyl, heterocycle, aryl or heteroaryl group; —SO₃H, the pharmaceutically-acceptable salts thereof, the pharmaceutically-acceptable alkyl esters thereof, the unsubstituted amide thereof, and the amide thereof substituted with one or two alkyl groups; —CO₂H, the pharmaceutically-acceptable salts thereof, the pharmaceutically-acceptable alkyl esters thereof, the unsubstituted amide thereof, and the amide thereof substituted with one or two alkyl groups; PO₃H₂, the pharmaceutically-acceptable salts thereof, the pharmaceutically-acceptable alkyl esters thereof, the unsubstituted amide thereof, and the amide thereof substituted with one or two alkyl groups; —(R⁸)PO₂H (where R⁸ is hydrogen or unsubstituted lower alkyl), the pharmaceutically-acceptable salts thereof, the pharmaceutically-acceptable alkyl esters thereof, the unsubstituted amide thereof, and the amide thereof substituted with one or two alkyl groups; aldehyde; ketone having an alkyl group; carbamate, unsubstituted or substituted with one or two alkyl groups; and combinations thereof; and wherein said substituted heterocycles are substituted halogen; nitro; cyano; heterocycle; aryl; heteroaryl; unsubstituted amino, the alkyl amides thereof, the heterocycle amides thereof, the aryl amides thereof, or the heteroaryl amides thereof; amino substituted with one alkyl, heterocycle, aryl or heteroaryl group and the alkyl amides thereof; amino substituted independently with one alkyl group and one alkyl group and one alkyl, heterocycle, aryl or heteroaryl group; hydroxy, the alkyl esters thereof, the heterocycle esters thereof, the aryl esters thereof, and the heteroaryl esters thereof; ether having an alkyl, heterocycle, aryl or heteroaryl group; thiol, alkyl thiol esters, heterocycle thiol esters, aryl thiol esters, and heteroaryl thiol esters; thioether having an alkyl, heterocycle, aryl or heteroaryl group; —SO₃H, the pharmaceutically-acceptable salts thereof, the pharmaceutically-acceptable alkyl esters thereof, the unsubstituted amide thereof, and the amide thereof substituted with one or two alkyl groups; —CO₂H, the pharmaceutically-acceptable salts thereof, the pharmaceutically-acceptable alkyl esters thereof, the unsubstituted amide thereof, and the amide thereof substituted with one or two alkyl groups; PO₃H₂, the pharmaceutically-acceptable salts thereof, the pharmaceutically-acceptable alkyl esters thereof, the unsubstituted amide thereof, and the amide thereof substituted with one or two alkyl groups; —(R⁸)PO₂H (where R⁸ is hydrogen or unsubstituted lower alkyl), the pharmaceutically-acceptable salts thereof, the pharmaceutically-acceptable esters thereof, the unsubstituted amide thereof, and the amide thereof substituted with one or two alkyl groups; aldehyde; ketone having an alkyl group; carbamate, unsubstituted or substituted with one or two alkyl groups; and combinations thereof; and wherein when the B moiety is substituted with a heterocycle, said heterocycle has 5 to 6 atoms in the ring and 1–3 heteroatoms selected from O, S, P or N; and wherein when the B moiety is substituted with an aryl, said aryls have 6–7 atoms in the ring; and wherein when the B moiety is substituted with a heteroaryl, said heteroaryl has 5 or 6 atoms in the ring and 1–3 heteroatoms selected from N, O, P or S;

(e) Z is unsubstituted or substituted pyridyl; wherein the Z moiety substituents are selected from the group consisting of halogen; lower alkyl; unsubstituted amino, and the lower alkyl amide thereof; amino substituted with one lower alkyl group, and the lower alkyl amide thereof; amino substituted independently with two lower alkyl groups; hydroxy, or the lower alkyl esters thereof; ether having a lower alkyl group; —CO²H, the pharmaceutically acceptable salts thereof, the pharmaceutically-acceptable lower alkyl esters thereof, the unsubstituted amide thereof, and the amide thereof substituted with one or two lower alkyl groups; nitro; and combinations thereof; and (f) each R¹ is independently selected from the group consisting of hydrogen, halogen, lower alkyl, unsubstituted amino or the lower alkyl amide thereof, amino substituted with one lower alkyl group or the lower alkyl amide thereof; amino independently substituted with two lower alkyl groups, hydroxy or the lower alkyl ester thereof, —CO₂H or the pharmaceutically-acceptable salts thereof or the pharmaceutically-acceptable lower alkyl esters thereof or the unsubstituted amide thereof or the amide thereof substituted with one or two lower alkyl groups, ether having a lower alkyl group, —PO₃H₂ or the pharmaceutically-acceptable salts thereof, and nitro, two R¹'s on the same carbon atom being =O or =NR⁹ (where R⁹ is unsubstituted lower alkyl or may be hydrogen when there is another nitrogen atom attached to the same carbon atom as the =NR⁹ moiety), and two R¹'s on adjacent carbon atoms being replaced by an additional bond between the carbon atoms;

and the pharmaceutically-acceptable salts thereof.

2. A compound of claim 1 wherein (a) m is an integer from 0 to 2;

(b) R is a moiety selected from the group consisting of hydrogen, unsubstituted lower alkyl, and substituted lower alkyl, wherein the substituents on said substituted lower alkyl are selected from the group consisting of halogen, unsubstituted and substituted phenyl, unsubstituted and substituted pyridinyl, unsubstituted amino, amino substituted with one or two lower alkyl groups, hydroxy and carboxy, and combinations thereof;

(c) B is hydrogen; and (d) each $R^1$ is independently selected from the group consisting of hydrogen, methyl, ethyl, hydroxy, unsubstituted amino, two $R^1$'s on the same carbon atom being $=O$ or $=NR^9$, and two $R^1$'s on adjacent carbon atoms being replaced by an additional bond between the carbon atoms.

3. A compound of claim 1 wherein (a) R is methyl;

(b) B is selected from the group consisting of hydrogen, methyl, ethyl, —$CO_2H$ and the pharmaceutically-acceptable salts thereof, —$CO_2CH_3$, and —$CONH_2$;

(c) Z is unsubstituted or mono-substituted with a substituent selected from the group consisting of methyl, ethyl, fluoro, chloro, bromo, trifluoromethyl, hydroxy, unsubstituted amino, (N-methyl)amino, (N,N-dimethyl)amino, methyl ether, —$CO_2H$ and the pharmaceutically-acceptable salts thereof, —$CO_2CH_3$, and —$CONH_2$;

(d) each $R^1$ is independently selected from the group consisting of hydrogen, methyl, ethyl, hydroxy, unsubstituted amino, two $R^1$'s on the same carbon atom being $=O$ or $=NR^9$, and two $R^1$'s on adjacent carbon atoms being replaced by an additional bond between the carbon atoms; and (e) $R^2$ is hydrogen, or $R^2$ is replaced by a second bond between the nitrogen and an adjacent atom.

4. A methylene phosphonoalkylphosphinic acid having the following structure:

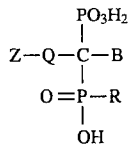

wherein (a) Q is $NR^2$; where $R^2$ is selected from the group consisting of hydrogen, lower alkyl, and lower alkyl acyl, or is replaced by a second bond between the nitrogen which it is on and an adjacent atom capable of accepting a second bond;

(b) R is a moiety selected from the group consisting of hydrogen and unsubstituted and substituted alkyl; wherein said substituents on the substituted alkyl include halogen, unsubstituted and substituted phenyl, unsubstituted and substituted pyridinyl, unsubstituted amino, amino substituted with one or two lower alkyl groups, hydroxy, carboxy, and chemically-stable combinations thereof;

(c) B is a moiety selected from the group consisting of hydrogen; unsubstituted and substituted lower alkyl; unsubstituted and substituted cycloalkyl having from 3 to 7 atoms in the ring; unsubstituted and substituted heterocycle having 5–7 atoms atoms in the ring 1–3 heteroatoms selected from O, P, S, or N; unsubstituted and substituted phenyl; —$CO_2H$, the pharmaceutically-acceptable salts thereof, the pharmaceutically-acceptable lower alkyl esters thereof, the unsubstituted amide thereof, and the amide thereof substituted with one or two lower alkyl groups;

wherein said substituted alkyls and substituted cycloalkyls are substituted with alkyl; halogen; nitro; cyano; heterocycle; aryl; heteroaryl; unsubstituted amino, the alkyl amides thereof, the heterocycle amides thereof, the aryl amides thereof, and the heteroaryl amides thereof; amino substituted with one alkyl, heterocycle, aryl or heteroaryl group and the alkyl amides thereof; amino substituted independently with one alkyl group and one alkyl, heterocycle, aryl or heteroaryl group; hydroxy, the alkyl esters thereof, the heterocycle esters thereof, the aryl esters thereof, and the heteroaryl esters thereof; ether having an alkyl, heterocycle, aryl or heteroaryl group; thiol, alkyl thiol esters, heterocycle thiol esters, aryl thiol esters, and heteroaryl thiol esters; thioether having an alkyl, heterocycle, aryl or heteroaryl group; —$SO_3H$, the pharmaceutically-acceptable salts thereof, the pharmaceutically-acceptable alkyl esters thereof, the unsubstituted amide thereof, and the amide thereof substituted with one or two alkyl groups; —$CO_2H$, the pharmaceutically-acceptable salts thereof, the pharmaceutically-acceptable alkyl esters thereof, the unsubstituted amide thereof, and the amide thereof substituted with one or two alkyl groups; $PO_3H_2$, the pharmaceutically-acceptable salts thereof, the pharmaceutically-acceptable alkyl esters thereof, the unsubstituted amide thereof, and the amide thereof substituted with one or two alkyl groups; —$(R^8)PO_2H$ (where $R^8$ is hydrogen or unsubstituted lower alkyl), the pharmaceutically-acceptable salts thereof, the pharmaceutically-acceptable alkyl esters thereof, the unsubstituted amide thereof, and the amide thereof substituted with one or two alkyl groups; aldehyde; ketone having an alkyl group; carbamate, unsubstituted or substituted with one or two alkyl groups; and combinations thereof; and wherein said substituted heterocycles are substituted halogen; nitro; cyano; heterocycle; aryl; heteroaryl; unsubstituted amino, the alkyl amides thereof, the heterocycle amides thereof, the aryl amides thereof, and the heteroaryl amides thereof; amino substituted with one alkyl, heterocycle, aryl or heteroaryl group and the alkyl amides thereof; amino substituted independently with one alkyl group and one alkyl, heterocycle, aryl or heteroaryl group; hydroxy, the alkyl esters thereof, the heterocycle esters thereof, the aryl esters thereof, and the heteroaryl esters thereof; ether having an alkyl, heterocycle, aryl or heteroaryl group; thiol, alkyl thiol esters, heterocycle thiol esters, aryl thiol esters, and heteroaryl thiol esters; thioether having an alkyl, heterocycle, aryl or heteroaryl group; —$SO_3H$, the pharmaceutically-acceptable salts thereof, the pharmaceutically-acceptable alkyl esters thereof, the unsubstituted amide thereof, and the amide thereof substituted with one or two alkyl groups; —$CO_2H$, the pharmaceutically-acceptable salts thereof, the pharmaceutically-acceptable alkyl esters thereof, the unsubstituted amide thereof, and the amide thereof substituted with one or two alkyl groups; $PO_3H_2$, the pharmaceutically-acceptable salts thereof, the pharmaceutically-acceptable alkyl esters thereof, the unsubstituted amide thereof, and the amide thereof substituted with one or two alkyl groups; —$(R^8)PO_2H$ (where $R^8$ is hydrogen or unsubstituted lower alkyl), the pharmaceutically-acceptable salts thereof, the pharmaceutically-acceptable esters thereof, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof; and wherein when the B moiety is substituted with a heterocycle, said heterocycle has 5 to 6 atoms in the ring and 1–3 heteroatoms selected from O, S, P or N; and wherein when the B moiety is substituted with an aryl, said aryls have 6–7 atoms in the ring; and wherein when the B moiety is substituted with a heteroaryl, said heteroaryl has 5 or 6 atoms in the ring and 1–3 heteroatoms selected from N, O, P or S;

(d) Z is unsubstituted or substituted pyridyl; wherein the substituents on the Z moiety are selected from the group consisting of halogen; lower alkyl; unsubstituted amino, and the lower alkyl amides thereof; amino substituted with one lower alkyl group, and the lower alkyl amides thereof; amino substituted independently with two lower alkyl groups; hydroxy, or the lower alkyl esters thereof; ether having a lower alkyl group; —$CO_2H$, the pharmaceutically acceptable salts thereof, the pharmaceutically-acceptable esters thereof, the unsubstituted amide thereof, and the amide thereof substituted with one or two lower alkyl groups; nitro; and combinations thereof; and (e) each $R^1$ is independently selected from the group consisting of hydrogen, halogen, lower alkyl, unsubstituted amino or the lower alkyl amide thereof, amino substituted with one lower alkyl group or the lower alkyl amide thereof, amino independently substituted with two lower alkyl groups, hydroxy or the lower alkyl ester thereof, —$CO_2H$ or the pharmaceutically-acceptable salts thereof or the pharmaceutically-acceptable lower alkyl esters thereof or the unsubstituted amide thereof or the amide thereof substituted with one or two lower alkyl groups, ether having a lower alkyl group, —$PO_3H_2$ or the pharmaceutically-acceptable salts thereof, and nitro, two $R^1$'s on the same carbon atom being =O or =$NR^9$ (where $R^9$ is unsubstituted lower alkyl or may be hydrogen when there is another nitrogen atom attached to the same carbon atom as the =$NR^9$ moiety), and two $R^1$'s on adjacent carbon atoms being replaced by an additional bond between the carbon atoms;

and the pharmaceutically-acceptable salts thereof.

5. A compound of claim 4 wherein (a) R is a moiety selected from the group consisting of hydrogen, unsubstituted lower alkyl, and substituted lower alkyl, wherein the substituents on said substituted lower alkyl are selected from the group consisting of halogen, unsubstituted and substituted phenyl, unsubstituted and substituted pyridinyl, unsubstituted amino, amino substituted with one or two lower alkyl groups, hydroxy and carboxy, and combinations thereof; and (b) B is hydrogen.

6. A compound of claim 5 wherein (a) R is methyl;

(b) B is selected from the group consisting of hydrogen, methyl, ethyl, —$CO_2H$ and the pharmaceutically-acceptable salts thereof, —$CO_2CH_3$, and —$CONH_2$;

(c) Z is unsubstituted or mono-substituted with a substituent selected from the group consisting of methyl, ethyl, fluoro, chloro, bromo, trifluoromethyl, hydroxy, (N-methyl)amino, (N,N-dimethyl)amino, methyl ether, —$CO_2H$ and the pharmaceutically-acceptable salts thereof, —$CO_2CH_3$, —$CONH_2$, and unsubstituted amino; and (d) $R^2$ is hydrogen, or $R^2$ is replaced by a second bond between the nitrogen and an adjacent atom.

7. A compound of claim 6 wherein Z is mono- or di-substituted independently with substituents selected from the group consisting of halogen, lower alkyl, unsubstituted amino and the acetyl amide thereof, amino substituted with one methyl group and the acetyl amide thereof, amino substituted with two methyl groups, hydroxy and the acetyl ester thereof, methyl ether, ethyl ether, —$CO_2H$ and the pharmaceutically-acceptable salts thereof, —$CO_2CH_3$, —$CO_2H_5$, —$CONH_2$, —$CONHCH_3$, —$CON(CH_3)_2$, nitro, and combinations thereof.

8. A compound of claim 5 wherein (a) R is unsubstituted, straight-chain, saturated lower alkyl; and (b) Z is unsubstituted or mono-substituted with a substituent selected from the group consisting of methyl, ethyl, chloro, bromo, hydroxy, unsubstituted amino, (N-methyl)amino, (N,N-dimethyl)amino, methyl ether, —$CO_2H$ and the pharmaceutically-acceptable salts thereof, —$CO_2CH_3$, and —$CONH_2$.

9. A compound of claim 8 wherein $R^2$ is hydrogen.

10. A compound of claim 9 wherein Q is attached to Z at the 2- position, and Z is unsubstituted or mono-substituted with methyl or amino at the 3-, 4- or 5- position.

11. A compound of claim 10 wherein Z is unsubstituted.

12. A compound of claim 10 wherein Z is monosubstituted with methyl at the 3- or 5- position.

13. A compound of claim 12 selected from the group consisting of N-(2'-(3'-methyl)-pyridinyl)aminomethane phosphonomethylphosphinate and N-(2'-5'-methyl)-pyridinyl)aminomethane phosphonomethylphosphinate.

14. A compound of claim 8 wherein Q is attached to Z at the 2- position by a double bond, and Z is unsubstituted or mono-substituted with methyl.

15. A compound of claim 14 wherein R is methyl.

16. A compound of claim 15 which is N-(2'-(3'-methyl)-piperidinylidene)aminomethane phosphonomethylphosphinate.

17. A pharmaceutical composition comprising:

(a) a safe and effective amount of a compound according to claim 1; and (b) a pharmaceutical carrier.

18. A pharmaceutical composition comprising:

(a) a safe and effective amount of a compound according to claim 4; and (b) a pharmaceutical carrier.

19. A pharmaceutical composition comprising:

(a) a safe and effective amount of a compound according to claim 7; and (b) a pharmaceutical carrier.

20. A pharmaceutical composition comprising:

(a) a safe and effective amount of a compound according to claim 8; and (b) a pharmaceutical carrier.

21. A pharmaceutical composition comprising:

(a) a safe and effective amount of a compound according to claim 16; and (b) a pharmaceutical carrier.

22. A method for treating a disease associated with abnormal calcium or phosphate metabolism in a human or other animal subject comprising administering to said subject a safe and effective amount of a compound of claim 1.

23. A method for treating a disease associated with abnormal calcium or phosphate metabolism in a human or other animal subject comprising administering to said subject a safe and effective amount of a compound of claim 4.

24. A method for treating a disease associated with abnormal calcium or phosphate metabolism in a human or other animal subject comprising administering to said subject a safe and effective amount of a compound of claim 7.

25. A method for treating a disease associated with abnormal calcium or phosphate metabolism in a human or other animal subject comprising administering to said subject a safe and effective amount of a compound of claim 8.

26. A method for treating a disease associated with abnormal calcium or phosphate metabolism in a human or other animal subject comprising administering to said subject a safe and effective amount of a compound of claim 16.

* * * * *